US008486966B2

(12) United States Patent
Davies et al.

(10) Patent No.: US 8,486,966 B2
(45) Date of Patent: Jul. 16, 2013

(54) 9-(PYRAZOL-3-YL)-9H-PURINE-2-AMINE AND 3-(PYRAZOL-3-YL) -3H-IMIDAZO[4,5-B] PYRIDIN-5-AMINE DERIVATIVES AND THEIR USE FOR THE TREATMENT OF CANCER

(75) Inventors: Audrey Davies, Waltham, MA (US); Stephanos Ioannidis, Waltham, MA (US); Michelle Lamb, Waltham, MA (US); Mei Su, Waltham, MA (US); Tao Wang, Waltham, MA (US); Hai-Jun Zhang, Waltham, MA (US)

(73) Assignee: Astrazeneca AB, Sodertalje (SE)

( * ) Notice: Subject to any disclaimer, the term of this patent is extended or adjusted under 35 U.S.C. 154(b) by 534 days.

(21) Appl. No.: 12/598,473

(22) PCT Filed: May 2, 2008

(86) PCT No.: PCT/GB2008/050321
§ 371 (c)(1),
(2), (4) Date: Apr. 16, 2010

(87) PCT Pub. No.: WO2008/135785
PCT Pub. Date: Nov. 13, 2008

(65) Prior Publication Data
US 2010/0324040 A1    Dec. 23, 2010

Related U.S. Application Data

(60) Provisional application No. 60/916,270, filed on May 4, 2007.

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)

(52) U.S. Cl.
USPC .......................................... 514/303; 546/118

(58) Field of Classification Search
USPC ........ 544/277, 333, 118; 546/118; 514/234.2, 514/303, 263.21, 256
See application file for complete search history.

(56) References Cited

U.S. PATENT DOCUMENTS

| | | | |
|---|---|---|---|
| 3,897,443 A | 7/1975 | Sharpe | |
| 4,038,240 A | 7/1977 | Hugl et al. | |
| 4,485,284 A | 11/1984 | Pakulis | |
| 5,147,876 A | 9/1992 | Mizuchi et al. | |
| 5,459,318 A | 10/1995 | Cacho et al. | |
| 5,521,184 A | 5/1996 | Zimmermann | |
| 6,383,553 B1 | 5/2002 | Tondar et al. | |
| 6,399,780 B1 | 6/2002 | Hudkins | |
| 6,455,525 B1 | 9/2002 | Singh et al. | |
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,660,731 B2 | 12/2003 | Bebbington et al. | |
| 6,664,247 B2 | 12/2003 | Bebbington et al. | |
| 6,696,452 B2 | 2/2004 | Davies et al. | |
| 6,727,251 B2 | 4/2004 | Bebbington et al. | |
| 6,989,385 B2 | 1/2006 | Bebbington et al. | |
| 7,008,948 B2 | 3/2006 | Bebbington et al. | |
| 7,087,603 B2 | 8/2006 | Bebbington et al. | |
| 7,098,330 B2 | 8/2006 | Bebbington et al. | |
| 7,115,739 B2 | 10/2006 | Bebbington et al. | |
| 7,148,455 B2 | 12/2006 | Scalese et al. | |
| 7,183,307 B2 | 2/2007 | Hale et al. | |
| 7,279,476 B2 | 10/2007 | Tang et al. | |
| 7,390,815 B2 | 6/2008 | Davies et al. | |

(Continued)

FOREIGN PATENT DOCUMENTS

| | | |
|---|---|---|
| EP | 0401358 | 12/1990 |
| EP | 1317448 | 5/2005 |

(Continued)

OTHER PUBLICATIONS ( Marotta et al., The journal of clinical investigation, (2011), vol. 121(7), pp. 2723-2735.*
Aimone et al. "Antinociceptive Activity of Selective Tyrosine Kinase Inhibitors in the Rat". Abstracts of the Annual Meeting of the Society for Neuroscience (2000), vol. 26, No. 1-2, 1692, XP008129558.
Alferez et al. "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Abstract 471.
Alferez et al. "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Poster.

(Continued)

*Primary Examiner* — Niloofar Rahmani

(57) ABSTRACT

The present invention relates to compounds of Formula (I): and to their pharmaceutical compositions, and to their methods of use. These compounds provide a treatment for myeloproliferative disorders and cancer.

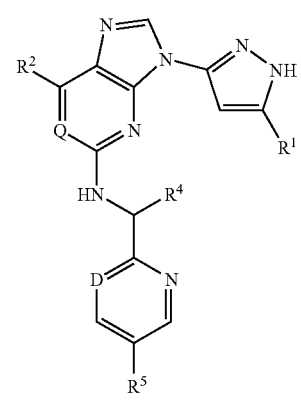

Formula (I)

4 Claims, No Drawings

U.S. PATENT DOCUMENTS

| | | | |
|---|---|---|---|
| 7,427,681 B2 | 9/2008 | Bebbington et al. | |
| 7,473,691 B2 | 1/2009 | Davies et al. | |
| 7,521,453 B2 | 4/2009 | Barlaam et al. | |
| 7,528,138 B2 | 5/2009 | Knegtel et al. | |
| 7,528,142 B2 | 5/2009 | Binch et al. | |
| 7,531,536 B2 | 5/2009 | Bebbington et al. | |
| 8,129,403 B2 * | 3/2012 | Lamb et al. | 514/300 |
| 2003/0055068 A1 | 3/2003 | Bebbington et al. | |
| 2003/0078275 A1 | 4/2003 | Bebbington et al. | |
| 2003/0079365 A1 | 5/2003 | Corak et al. | |
| 2003/0105090 A1 | 6/2003 | Bebbington et al. | |
| 2005/0038023 A1 | 2/2005 | Bebbington et al. | |
| 2005/0054638 A1 | 3/2005 | Barlaam et al. | |
| 2007/0142413 A1 | 6/2007 | Block et al. | |
| 2008/0004302 A1 | 1/2008 | Theoclitou et al. | |
| 2008/0108633 A1 | 5/2008 | Claesson | |
| 2008/0108669 A1 | 5/2008 | Claesson | |
| 2008/0176872 A1 | 7/2008 | Lamb et al. | |
| 2008/0194606 A1 | 8/2008 | Scott et al. | |
| 2008/0287437 A1 | 11/2008 | Wang et al. | |
| 2008/0287475 A1 | 11/2008 | Feng et al. | |
| 2009/0005396 A1 | 1/2009 | Claesson | |
| 2010/0152219 A1 | 6/2010 | Block et al. | |
| 2012/0122892 A1 * | 5/2012 | Lamb et al. | 514/261.1 |

FOREIGN PATENT DOCUMENTS

| | | |
|---|---|---|
| EP | 1317444 | 5/2006 |
| EP | 1317447 | 5/2006 |
| EP | 1317449 | 5/2006 |
| EP | 1317452 | 5/2006 |
| EP | 1318997 | 5/2006 |
| EP | 1345922 | 5/2006 |
| EP | 1345926 | 5/2006 |
| EP | 1345927 | 5/2006 |
| EP | 1345929 | 5/2006 |
| EP | 1353916 | 9/2006 |
| EP | 1345928 | 2/2007 |
| EP | 1876178 | 1/2008 |
| EP | 1686999 | 7/2009 |
| JP | 2003231687 | 8/2003 |
| WO | WO 95/09852 | 4/1995 |
| WO | WO 97/09325 | 3/1997 |
| WO | WO 97/19065 | 5/1997 |
| WO | WO 97/22596 | 6/1997 |
| WO | WO 97/30035 | 8/1997 |
| WO | WO 97/32856 | 9/1997 |
| WO | WO 98/13354 | 4/1998 |
| WO | WO 98/38171 | 9/1998 |
| WO | WO 99/02166 | 1/1999 |
| WO | WO 99/41253 | 8/1999 |
| WO | WO 00/12485 | 3/2000 |
| WO | WO 00/14552 | 3/2000 |
| WO | WO 00/16067 | 3/2000 |
| WO | WO 00/27825 | 5/2000 |
| WO | WO 00/35455 | 6/2000 |
| WO | WO 00/39101 | 7/2000 |
| WO | WO 00/40529 | 7/2000 |
| WO | WO 00/41669 | 7/2000 |
| WO | WO 00/53595 | 9/2000 |
| WO | WO 00/63182 | 10/2000 |
| WO | WO 00/73344 | 12/2000 |
| WO | WO 00/78731 | 12/2000 |
| WO | WO 01/14380 | 3/2001 |
| WO | WO 01/17995 | 3/2001 |
| WO | WO 01/22938 | 4/2001 |
| WO | WO 01/47921 | 7/2001 |
| WO | WO 01/60816 | 8/2001 |
| WO | WO 01/64655 | 9/2001 |
| WO | WO 01/64656 | 9/2001 |
| WO | WO 01/85699 | 11/2001 |
| WO | WO 01/92224 | 12/2001 |
| WO | WO 02/04434 | 1/2002 |
| WO | WO 02/08213 | 1/2002 |
| WO | WO 02/18346 | 3/2002 |
| WO | WO 02/20479 | 3/2002 |
| WO | WO 02/20513 | 3/2002 |
| WO | WO 02/22601 | 3/2002 |
| WO | WO 02/22602 | 3/2002 |
| WO | WO 02/22603 | 3/2002 |
| WO | WO 02/22604 | 3/2002 |
| WO | WO 02/22605 | 3/2002 |
| WO | WO 02/22606 | 3/2002 |
| WO | WO 02/22607 | 3/2002 |
| WO | WO 02/22608 | 3/2002 |
| WO | WO 02/50065 | 6/2002 |
| WO | WO 02/50066 | 6/2002 |
| WO | WO 02/50071 | 6/2002 |
| WO | WO 02/059111 | 8/2002 |
| WO | WO 02/062789 | 8/2002 |
| WO | WO 02/064096 | 8/2002 |
| WO | WO 02/092571 | 11/2002 |
| WO | WO 03/026665 | 4/2003 |
| WO | WO 03/027111 | 4/2003 |
| WO | WO 03/048133 | 6/2003 |
| WO | WO 2004/037814 | 5/2004 |
| WO | WO 2005/016893 | 2/2005 |
| WO | WO 2005/048133 | 5/2005 |
| WO | WO 2005/049033 | 6/2005 |
| WO | WO 2005/095400 | 10/2005 |
| WO | WO 2005/103010 | 11/2005 |
| WO | WO 2005/105814 | 11/2005 |
| WO | WO 2006/037117 | 4/2006 |
| WO | WO 2006/048080 | 5/2006 |
| WO | WO 2006/067614 | 6/2006 |
| WO | WO 2006/074057 | 7/2006 |
| WO | 2006087530 | * 8/2006 |
| WO | WO 2006/082392 | 8/2006 |
| WO | WO 2006/087530 | 8/2006 |
| WO | WO 2006/087538 | 8/2006 |
| WO | WO 2006/115452 | 11/2006 |
| WO | WO 2006/123113 | 11/2006 |
| WO | WO 2007/049041 | 5/2007 |
| WO | WO 2007/071348 | 6/2007 |
| WO | WO 2008/005538 | 1/2008 |
| WO | WO 2008/135785 | 11/2008 |
| WO | WO 2010/038060 | 4/2010 |

OTHER PUBLICATIONS

Blowers "AZD8931". IASLC Annual Targeted Therapies of the Treatment of Lung Cancer Meeting (2011), Santa Monica, CA, PowerPoint Presentation.

Breault et al. "Cyclin-Dependent Kinase 4 Inhibitors as a Treatment for Cancer. Part 2: Identification and Optimisation of Substituted 2, 4-Bis Anilino Pyrimidines". Bioorganic & Medicinal Chemistry Letters (2003), vol. 13, 2961-2966.

Cristofanilli et al. "Exploratory Subset Analysis According to Prior Endocrine Treatment of Two Randomized Phase II Trials Comparing Gefitinib (G) with Placebo (P) in Combination with Tamoxifen (T) or Anastrozole (A) in Hormone Receptor-Positive (HR+) Metastatic Breast Cancer (MBC)". J Clin. Oncol. (2009), vol. 27, 15s, Abstract 1014.

El Kerdaway et al. "2, 4-Bis (substituted)-5-nitropyrimidines of Expected Diuretic Action". Egypt J. Chem (1986), vol. 92, No. 2, 247-251.

Hefti et al. "Novel Class of Pain Drugs Based on Antagonism of NGF". Trends in Pharmacological Sciences (2006), vol. 27, No. 2, 85-91.

Hickinson et al. "AZD8931, an Equipotent, Reversible Inhibitor of Signaling by Epidermal Growht Factor Receptor, ERBB2 (HER2), and ERBB3: A Unique Agent for Simultaneous ERBB Receptor Blockage in Cancer". Clinical Cancer Research (2010) vol. 16, 1159-1169.

International Search Report for corresponding PCT application No. PCT/GB2006/000334.

Keilholz et al. "Phase I Dose-Finding Study of Monotherapy with AZD8931, an Inhibitor of erbB1, 2 and 3 Signaling, in Patients with Advanced Solid Tumors". J Clin Oncol. (2011), vol. 29, Abstract 3097.

Keilholz et al. "Phase I Dose-Finding Study of Monotherapy with AZD8931, an Inhibitor of erbB1, 2 and 3 Signaling, in Patients with Advanced Solid Tumors". ASCO (2011), Poster.

Klinowska et al. "AZD8931, an Equipotent, Reversible Inhibitor of erbB1, erbB2 and erbB3 Receptor Signaling: Characterisation of Pharmacological Profile". European Journal of Cancer Supplements (2009), vol. 7, No. 2, 127.

Leroith and Roberts. "The Insulin-Like Growth Factor System and Cancer". Cancer Letters (2003), vol. 195, 127-137.

Lopez-Martin et al. "Phase I Dose-Finding Study of AZD8931, an Inhibitor of erbB1, 2 and 3 Receptor Signaling, in Combination with Paclitaxel". J Clin. Oncol. (2011), vol. 29, Abstract 3105.

Lopez-Martin et al. "Phase I Dose-Finding Study of AZD8931, an Inhibitor of erbB1, 2 and 3 Receptor Signaling, in Combination with Paclitaxel". ASCO (2011), Poster.

Marshall et al. "Evaluation of AZD8931, an Equipotent Inhibitor of erbB1, erbB2 and erbB3 Receptor Signaling, on Ligand Stimulated Breast Cancer Cell Lines with Differing Levels of erbB2 Expression". SABCS (2009), Abstract 5059.

Normanno et al. "Target-based therapies in breast cancer: current status and future perspectives". Endocr Relat Cancer (2009), vol. 16(3): 675-702.

Parrizas et al. "Specific Inhibition of Insulin-Like Growth Factor-1 and Insulin Receptor Tyrosine Kinase Activity and Biological Function by Tyrphostins". Endocrinology (1997), vol. 138, No. 4, 1427-1433.

Pierce et al. "CH . . . O and CH . . . N Hydrogen Bonds in Ligand Design: A Novel Quinazolin-4-ylthiazol-2-ylamine Protein Kinase Inhibitor". J. Med. Chem. (2005), vol. 48, 1278-1281.

Simone "Cecil Textbook of Medicine", 20th Editon, Oncology: Introduction (1996), vol. 1, 1004-1010.

Speake et al. "Characterization of AZD8931, a Potent Reversible Small Molecule Inhibitor Against Epidermal Growth Factor Receptor (EGFR), Erythroblastic Leukemia Viral Oncogene Homolog 2 (HER2) and 3 (HER3) with a Unique and Balanced Pharmacological Profile". J Clin. Oncol. (2009), vol. 27, 15s, Abstract 11072.

Thress et al. "Identification and Preclinical Characterization of AZ-23, a Novel, Selective, and Orally Bioavailable Inhibitor of the Trk Kinase Pathway". Molecular Cancer Therapeutics (2009) vol. 8, No. 7, 1818-1827.

Ulrich et al. "Chapter 4: Crystallization". Kirk-Othmer Encyclopedia of Chemical Technology (Aug. 2002).

Vippagunta et al. "Crystalline Solids". Advanced Drug Delivery Reviews (2001), vol. 48, 3-26.

Wang et al. "Identification of 4-Aminopyrazolylpyrimidines as Potent Inhibitors of Trk Kinases". J. Med. Chem. (2008), vol. 51, No. 15, 4672-4684, ACS Publications, DC, US.

Wang et al. "Trik Kinase Inhibitors as New Treatments for Cancer and Pain". Expert Opin. Ther. Patents (2009), vol. 19, No. 3, 305-319.

West "Chapter 10: Solid Solutions". Solid State Chemistry and Its Applications (1988), 358 & 365.

Winston et al. "Suppression of Neuronal Tyrosine Kinase Activity in Associated with Improvement in Pain Responses and Inhibition of Nociceptive Gene Expression in Pancreatitis". Abstracts of the Annual Meeting of the Society for Neuroscience (2001), vol. 27, 2162, XP008129567.

Changelian et al., "Prevention of Organ Allograft Rejection by a Specific Janus Kinase 3 Inhibitor", Science 302: 875-878 (2003).

George et al., "Sustained in Vivo Regression of Dunning H Rat Prostate Cancers Treated with Combinations of Androgen Ablation and Trk Tyrosine Kinase Inhibitors, CEP-751 (KT-6587) or CEP-701 (KT-5555)", Cancer Research 59: 2395-2401 (1999).

Thompson et al., "Photochemical Preparation of a Pyridone Containing Tetracycle: A JAK Protein Kinase Inhibitor", Bioorganic Medicinal Chemistry Letters 12: 1219-1223 (2002).

Wolfe et al., "Room Temperature Catalytic Amination of Aryl Iodides", Journal of Organic Chemistry 62: 6066-6068 (1997).

Wolfe et al., "An Improved Catalyst System for Aromatic Carbon-Nitrogen Bond Formation: The Possible Involvement of Bis(Phosphine) Palladium Complexes as Key Intermediates", Journal of the American Chemical Society 118: 7215-7216 (1996).

Marcoux et al., "Palladium-Catalyzed Amination of Aryl Bromides: Use of Phosphinoether Ligands for the Efficient Coupling of Acyclic Secondary Amines", Journal of Organic Chemistry 62: 1568-1569 (1997).

Wagaw et al., "Palladium-Catalyzed Coupling of Optically Active Amines with Aryl Bromides", Journal of the American Chemical Society 119: 8451-8458 (1997).

Lippa et al., "Discovery of Novel Isothiazole Inhibitors of the TrkA Kinase: Structure-Activity Relationship, Computer Modeling, Optimization, and Identification of Highly Potent Antagonists", Bioorganic & Medicinal Chemistry Letters 16: 3444-3448 (2006).

Weeraratna et al., "Rational Basis for Trk Inhibition Therapy for Prostate Cancer", The Prostate 45: 140-148 (2000).

Patapoutian, "Trk Receptors: Mediators of Neurotrophin Action", Current Opinion in Neurobiology 11: 272-280, (2001).

Davidson et al., "Expression and Activation of the Nerve Growth Factor Receptor TrkA in Serous Ovarian Carcinoma", Clinical Cancer Research 9: 2248-2259 (2003).

Tibes et al., "Tyrosine Kinase Inhibitors and the Dawn of Molecular Cancer Therapeutics", Annual Review Pharmacol. Toxicol. 45: 357-384 (2005).

Sordella et al., "Gefitinib-Sensitizing EGFR Mutations in Lung Cancer Activate Anti-Apoptotic Pathways", Science 305: 1163-1167 (2004).

Tan et al., "Suppressors of Cytokine Signaling in Health and Disease", Pediatric Nephrology 20: 567-575 (2005).

Tognon et al., "Expression of the ETV6-NTRK3 Gene Fusion as a Primary Event in Human Secretory Breast Carcinoma", Cancer Cell 2: 367-376 (2002).

Bardelli et al., "Mutational Analysis of the Tyrosine Kinome in Colorectal Cancers", Science 300: 949 (2003).

Percy, "The V617F JAK2 Mutation and the Myeloproliferative Disorders", Hematological Oncology 23: 91-93 (2005).

Verma et al., "Jak Family of Kinases in Cancer", Cancer and Metastasis Reviews 22: 423-434 (2003).

Marotta et al., "The JAK2/STAT3 Signaling Pathway is Required for Growth of CD44+CD24-Stem Cell—Like Breast Cancer Cells in Human Tumors", The Journal of Clinical Investigation 121(7): 2723-2735 (2011).

* cited by examiner

US 8,486,966 B2

9-(PYRAZOL-3-YL)-9H-PURINE-2-AMINE AND 3-(PYRAZOL-3-YL)-3H-IMIDAZO[4,5-B] PYRIDIN-5-AMINE DERIVATIVES AND THEIR USE FOR THE TREATMENT OF CANCER

CROSS-REFERENCE TO RELATED APPLICATIONS

This application is a US National Stage under 35 U.S.C. §371 of International Application No. PCT/GB2008/050321 (filed May 2, 2008) which claims priority under 35 U.S.C. §119(e) to U.S. Provisional Application No. 60/916,270 (filed on May 4, 2007).

FIELD OF THE INVENTION

The present invention relates to a novel compound, its pharmaceutical compositions and methods of use. In addition, the present invention relates to therapeutic methods for the treatment and prevention of cancers and to the use of this compound in the manufacture of medicaments for use in the treatment and prevention of myeloproliferative disorders and cancers.

BACKGROUND OF THE INVENTION

Receptor tyrosine kinases (RTK's) are a sub-family of protein kinases that play a critical role in cell signalling and are involved in a variety of cancer related processes including cell proliferation, survival, angiogenesis and metastasis. Currently up to 100 different RTK's including tropomyosin-related kinases (Trk's) have been identified.

Trk's are the high affinity receptors activated by a group of soluble growth factors called neurotrophins (NT). The Trk receptor family has three members—TrkA, TrkB and TrkC. Among the NTs there are (i) nerve growth factor (NGF) which activates TrkA, (ii) brain-derived growth factor (BDNF) and NT-4/5 which activate TrkB and (iii) NT3 which activates TrkC. Each Trk receptor contains an extra-cellular domain (ligand binding), a trans-membrane region and an intra-cellular domain (including kinase domain). Upon binding of the ligand, the kinase catalyzes auto-phosphorylation and triggers downstream signal transduction pathways.

Trk's are widely expressed in neuronal tissue during its development where Trk's are critical for the maintenance and survival of these cells. A post-embryonic role for the Trk/neurotrophin axis (or pathway), however, remains in question. There are reports showing that Trk's play important role in both development and function of the nervous system (Patapoutian, A. et al Current Opinion in Neurobiology, 2001, 11, 272-280).

In the past decade, a considerable number of literature documentations linking Trk signalling with cancer have published. For example, while Trk's are expressed at low levels outside the nervous system in the adult, Trk expression is increased in late stage prostate cancers. Both normal prostate tissue and androgen-dependent prostate tumors express low levels of Trk A and undetectable levels of Trk B and C. However, all isoforms of Trk receptors as well as their cognate ligands are up-regulated in late stage, androgen-independent prostate cancer. There is additional evidence that these late stage prostate cancer cells become dependent on the Trk/neurotrophin axis for their survival. Therefore, Trk inhibitors may yield a class of apoptosis-inducing agents specific for androgen-independent prostate cancer (Weeratna, A. T. et al The Prostate, 2000, 45, 140-148).

Furthermore, the literature also shows that over-expression, activation, amplification and/or mutation of Trk's are associated with secretory breast carcinoma (Cancer Cell, 2002, 2, 367-376), colorectal cancer (Bardelli et al Science, 2003, 300, 949-949) and ovarian cancer (Davidson, B. et al Clinical Cancer Research, 2003, 9, 2248-2259).

There are a few reports of selective Trk tyrosine kinase inhibitors. Cephalon described CEP-751, CEP-701 (George, D. et al Cancer Research, 1999, 59, 2395-2341) and other indolocarbazole analogues (WO0114380) as Trk inhibitors. It was shown that CEP-701 and/or CEP751, when combined with surgically or chemically induced androgen ablation, offered better efficacy compared with mono-therapy alone. GlaxoSmithKline disclosed certain oxindole compounds as Trk A inhibitors in WO0220479 and WO0220513. Recently, Japan Tobacco reported pyrazolyl condensed cyclic compounds as Trk inhibitors (JP2003231687A). Pfizer also recently published certain isothiazole Trk A inhibitors (Bioorg. Med. Chem. Lett. 2006, 16, 3444-3448).

In addition to the above, Vertex Pharmaceuticals have described pyrazole compounds as inhibitors of GSK3, Aurora, etc. in WO0250065, WO0262789, WO03027111 and WO200437814; and AstraZeneca have reported pyrazole compounds as inhibitors against IGF-1 receptor kinase (WO0348133). AstraZeneca have also reported Trk inhibitors in International Applications WO 2005/049033, WO 2005/103010, WO 2006/082392, WO 2006/087530, and WO 2006/087538.

Another such family of RTK's is the JAK family. The JAK (Janus-associated kinase)/STAT (signal transducers and activators or transcription) signalling pathway is involved in a variety of hyperproliferative and cancer related processes including cell-cycle progression, apoptosis, angiogenesis, invasion, metastasis and evasion of the immune system (Haura et al., Nature Clinical Practice Oncology, 2005, 2(6), 315-324; Verna et al., Cancer and Metastasis Reviews, 2003, 22, 423-434).

The JAK family consists of four non-receptor tyrosine kinases Tyk2, JAK1, JAK2, and JAK3, which play a critical role in cytokine- and growth factor mediated signal transduction. Cytokine and/or growth factor binding to cell-surface receptor(s), promotes receptor dimerization and facilitates activation of receptor-associated JAK by autophosphorylation. Activated JAK phosphorylates the receptor, creating docking sites for SH2 domain-containing signalling proteins, in particular the STAT family of proteins (STAT1, 2, 3, 4, 5a, 5b and 6). Receptor-bound STATs are themselves phosphorylated by JAKs, promoting their dissociation from the receptor, and subsequent dimerization and translocation to the nucleus. Once in the nucleus, the STATs bind DNA and cooperate with other transcription factors to regulate expression of a number of genes including, but not limited to, genes encoding apoptosis inhibitors (e.g. Bcl-XL, Mcl-1) and cell cycle regulators (e.g. Cyclin D1/D2, c-myc) (Haura et al., Nature Clinical Practice Oncology, 2005, 2(6), 315-324; Verna et al., Cancer and Metastasis Reviews, 2003, 22, 423-434).

Over the past decade, a considerable amount of scientific literature linking constitutive JAK and/or STAT signalling with hyperproliferative disorders and cancer has been published. Constitutive activation of the STAT family, in particular STAT3 and STAT5, has been detected in a wide range of cancers and hyperproliferative disorders (Haura et al., Nature Clinical Practice Oncology, 2005, 2(6), 315-324). Furthermore, aberrant activation of the JAK/STAT pathway provides an important proliferative and/or anti-apoptotic drive downstream of many kinases (e.g. Flt3, EGFR) whose constitutive activation have been implicated as key drivers in a variety of cancers and hyperproliferative disorders (Tibes et al., Annu Rev Pharmacol Toxicol 2550, 45, 357-384; Choudhary et al., International Journal of Hematology 2005, 82(2), 93-99; Sordella et al., Science 2004, 305, 1163-1167). In addition, impairment of negative regulatory proteins, such as the suppressors of cytokine signalling (SOCS) proteins, can also influence the activation status of the JAK/STAT signalling pathway in disease (JC Tan and Rabkin R, Pediatric Nephrology 2005, 20, 567-575).

Several mutated forms of JAK2 have been identified in a variety of disease settings. For example, translocations resulting in the fusion of the JAK2 kinase domain with an oligomerization domain, TEL-JAK2, Bcr-JAK2 and PCM1-JAK2, have been implicated in the pathogenesis of various hematologic malignancies (SD Turner and Alesander D R, Leukemia, 2006, 20, 572-582). More recently, a unique acquired mutation encoding a valine-to-phenylalanine (V617F) substitution in JAK2 was detected in a significant number of polycythemia vera, essential thrombocythemia and idiopathic myelofibrosis patients and to a lesser extent in several other diseases. The mutant JAK2 protein is able to activate downstream signalling in the absence of cytokine stimulation, resulting in autonomous growth and/or hypersensitivity to cytokines and is believed to play a critical role in driving these diseases (M J Percy and McMullin M F, Hematological Oncology 2005, 23(3-4), 91-93).

JAKs (in particular JAK3) play an important biological roles in the immunosuppressive field and there are reports of using JAK kinase inhibitors as tools to prevent organ transplant rejections (Changelian, P. S. et al, Science, 2003, 302, 875-878). Merck (Thompson, J. E. et al Bioorg. Med. Chem. Lett. 2002, 12, 1219-1223) and Incyte (WO2005/105814) reported imidazole based JAK2/3 inhibitors with enzyme potency at single nM levels. Recent Vertex PCT publications have described azaindoles as JAK inhibitors (WO2005/95400). AstraZeneca has published quinoline-3-carboxamides as JAK3 inhibitors (WO2002/92571).

In addition to the above, Vertex Pharmaceuticals has described pyrazole compounds as inhibitors of GSK3, Aurora, etc. in WO2002/50065, WO2002/62789, WO2003/027111 and WO2004/37814; and AstraZeneca has reported pyrazole compounds as inhibitors against IGF-1 receptor kinase—WO2003/48133- and Trk in WO2005/049033, WO2005/103010, WO2006/082392.

SUMMARY OF THE INVENTION

In accordance with the present invention, the applicants have hereby discovered novel compounds of Formula (I):

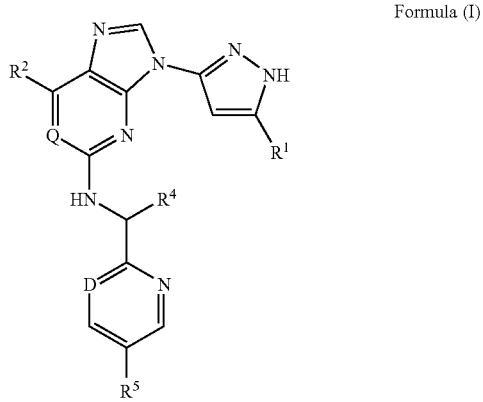

Formula (I)

or pharmaceutically acceptable salts thereof.

It is believed that the compounds of Formula (I), or pharmaceutically acceptable salts thereof, possess beneficial efficacious, metabolic, and/or pharmacodynamic properties.

The compounds of Formula (I), or pharmaceutically acceptable salts thereof, are believed to possess Trk kinase inhibitory activity and are accordingly useful for their anti-proliferation and/or proapoptotic (such as anti-cancer) activity and in methods of treatment of the human or animal body.

The invention also relates to processes for the manufacture of said compounds, or pharmaceutically acceptable salts thereof, to pharmaceutical compositions containing them and to their use in the manufacture of medicaments for use in the production of an anti-proliferation and/or proapoptotic effect in warm-blooded animals such as man.

Also in accordance with the present invention the applicants provide methods of using such compounds, or pharmaceutically acceptable salts thereof, in the treatment of cancer.

The properties of the compounds of Formula (I), or pharmaceutically acceptable salts thereof, are expected to be of value in the treatment of disease states associated with cell proliferation such as cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Furthermore, the compounds of Formula (I), or pharmaceutically acceptable salts thereof, are expected to be of value in the treatment or prophylaxis of cancers selected from congenital fibrosarcoma, mesoblastic nephroma, mesothelioma, acute myeloblastic leukemia, acute lymphocytic leukemia, multiple myeloma, melanoma, oesophageal cancer, myeloma, hepatocellular, pancreatic, cervical cancer, Ewings sarcoma, neuroblastoma, Kaposi sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma and leukaemia; particularly ovarian cancer, breast cancer, colorectal cancer, prostate cancer and lung cancer—NSCLC and SCLC; more particularly prostate cancer; and more particularly hormone refractory prostate cancer.

The compounds of Formula (I), or pharmaceutically acceptable salts thereof, are further believed to be of value in the treatment or prophylaxis of inflammatory disorders, including such conditions as: allergies, including allergic rhinitis/sinusitis, skin allergies (urticaria/hives, angioedema, atopic dermatitis), food allergies, drug allergies, insect allergies, and rare allergic disorders such as mastocytosis; asthma; Arthritis, including osteoarthritis, rheumatoid arthritis, and spondyloarthropathies; Autoimmune conditions, including systemic lupus erythematosus, dermatomyositis, polymyositis, inflammatory neuropathies (Guillain Barré, inflammatory polyneuropathies), Crohn's disease, ulcerative colitis, vasculitis (Wegener's granulomatosus, polyarteritis nodosa), and rare disorders such as polymyalgia rheumatica, temporal arteritis, Sjogren's syndrome, Bechet's disease, Churg-Strauss syndrome, and Takayasu's arteritis; cardiovascular inflammation; gastrointestinal inflammation; infection and immunity; leukocyte biology and immunology; neuroinflammatory disorders; and transplantation. Additionally, the compounds of Formula (I), or pharmaceutically acceptable salts thereof, are expected to be of value in the treatment or prophylaxis of persistent pain states, including neuropathic pain, and pain associated with inflammation.

The compounds of Formula (I), or pharmaceutically acceptable salts thereof, are also believed to possess JAK kinase inhibitory activity and are accordingly useful for their anti-proliferation and/or pro-apoptotic activity and in methods of treatment of the human or animal body. The invention also relates to processes for the manufacture of said compound, or pharmaceutically acceptable salts thereof, to pharmaceutical compositions containing it and to its use in the manufacture of medicaments for use in the production of an anti-proliferation and/or pro-apoptotic effect in warm-blooded animals such as man. Also in accordance with the present invention the applicants provide methods of using said compound, or pharmaceutically acceptable salts thereof, in the treatment of myeloproliferative disorders, myelodysplastic syndrome and cancer.

The properties of the compounds of Formula (I), or pharmaceutically acceptable salts thereof, are expected to be of value in the treatment of myeloproliferative disorders, myelodysplastic syndrome, and cancer by inhibiting the tyrosine kinases, particularly the JAK family and more particularly JAK2. Methods of treatment target tyrosine kinase activity, particularly the JAK family activity and more particularly JAK2 activity, which is involved in a variety of myeloproliferative disorders, myelodysplastic syndrome and cancer related processes. Thus, inhibitors of tyrosine kinases, particularly the JAK family and more particularly JAK2, are expected to be active against myeloproliferative disorders such as chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and neoplastic disease such as carcinoma of the breast, ovary, lung, colon, prostate or other tissues, as well as leukemias, myelomas and lymphomas, tumors of the central and peripheral nervous system, and other tumor types such as melanoma, fibrosarcoma and osteosarcoma. Tyrosine kinase inhibitors, particularly the JAK family inhibitors and more particularly JAK2 inhibitors are also expected to be useful for the treatment other proliferative diseases including but not limited to autoimmune, inflammatory, neurological, and cardiovascular diseases.

Furthermore, the compounds of Formula (I), or pharmaceutically acceptable salts thereof, are expected to be of value in the treatment or prophylaxis of against myeloproliferative disorders selected from chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and cancers selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma and leukaemia; particularly myeloma, leukemia, ovarian cancer, breast cancer and prostate cancer.

DETAILED DESCRIPTION

The present invention provides compounds of Formula (I):

Formula (I)

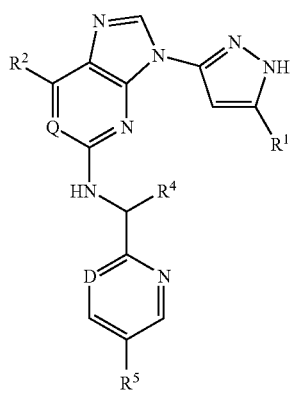

or pharmaceutically acceptable salts thereof, wherein
Q may be selected from N and $C(R^3)$;
D may be selected from N and CH;
$R^1$ may be selected from H, —CN, $C_{1-6}$alkyl, $C_{2-6}$alkenyl, $C_{2-6}$alkynyl, 3- to 5-membered carbocyclyl, 5-membered heterocyclyl, —$OR^{1a}$, —$SR^{1a}$, —$N(R^{1a})_2$, —$N(R^{1a})C(O)R^{1b}$, —$N(R^{1a})N(R^{1a})_2$, —$NO_2$, —C(O)H, —$C(O)R^{1b}$, —$C(O)_2R^{1a}$, —$C(O)N(R^{1a})_2$, —$OC(O)N(R^{1a})_2$, —$N(R^{1a})C(O)_2R^{1a}$, —$N(R^{1a})C(O)N(R^{1a})_2$, —$OC(O)R^{1b}$, —$S(O)R^{1b}$, —$S(O)_2R^{1b}$, —$S(O)_2N(R^{1a})_2$, —$N(R^{1a})S(O)_2R^{1b}$, —$C(R^{1a})$=$N(R^{1a})$, and —$C(R^{1a})$=$N(OR^{1a})$, wherein said $C_{1-6}$alkyl, $C_{2-6}$alkenyl, $C_{2-6}$alkynyl, 3- to 5-membered carbocyclyl, and 5-membered heterocyclyl may be optionally substituted with one or more $R^{10}$;
$R^{1a}$ in each occurrence may be independently selected from H and $C_{1-6}$alkyl, 3- to 5-membered carbocyclyl, and 5-membered heterocyclyl, wherein said $C_{1-6}$alkyl, 3- to 5-membered carbocyclyl, and 5-membered heterocyclyl in each occurrence may be optionally and independently substituted with one or more $R^{10}$;
$R^{1b}$ in each occurrence may be independently selected from $C_{1-6}$alkyl, $C_{2-6}$alkenyl, $C_{2-6}$alkynyl, 3- to 5-membered carbocyclyl, and 5-membered heterocyclyl, wherein said $C_{1-6}$alkyl, $C_{2-6}$alkenyl, $C_{2-6}$alkynyl, 3- to 5-membered carbocyclyl, and 5-membered heterocyclyl in each occurrence may be optionally and independently substituted with one or more $R^{10}$;
$R^2$ may be selected from H, halo, —CN, $C_{1-6}$alkyl, $C_{2-6}$alkenyl, $C_{2-6}$alkynyl, carbocyclyl, heterocyclyl, —$OR^{2a}$, —$SR^{2a}$, —$N(R^{2a})_2$, —$N(R^{2a})C(O)R^{2b}$, —$N(R^{2a})N(R^{2a})_2$, —$NO_2$, —C(O)H, —$C(O)R^{2b}$, —$C(O)_2R^{2a}$, —$C(O)N(R^{2a})_2$, —$OC(O)N(R^{2a})_2$, —$N(R^{2a})C(O)_2R^{2a}$, —$N(R^{2a})C(O)N(R^{2a})_2$, —$OC(O)R^{2b}$, —$S(O)R^{2b}$, —$S(O)_2R^{2b}$, —$S(O)_2N(R^{2a})_2$, —$N(R^{2a})S(O)_2R^{2b}$, —$C(R^{2a})$=$N(R^{2a})$, and —$C(R^{2a})$=$N(OR^{2a})$, wherein said $C_{1-6}$alkyl, $C_{2-6}$alkenyl, $C_{2-6}$alkynyl, carbocyclyl, and heterocyclyl may be optionally substituted with one or more $R^{20}$;
$R^{2a}$ in each occurrence may be independently selected from H, $C_{1-6}$alkyl, carbocyclyl, and heterocyclyl, wherein said $C_{1-6}$alkyl, carbocyclyl, and heterocyclyl in each occurrence may be optionally and independently substituted with one or more $R^{20}$;
$R^{2b}$ in each occurrence may be independently selected from $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence may be optionally and independently substituted with one or more $R^{20}$;
$R^3$ may be selected from H, halo, —CN, $C_{1-6}$alkyl, $C_{2-6}$alkenyl, $C_{2-6}$alkynyl, carbocyclyl, heterocyclyl, —$OR^{3a}$, —$SR^{3a}$, —$N(R^{3a})_2$, —$N(R^{3a})C(O)R^{3b}$, —$N(R^{3a})N(R^{3a})_2$, —$NO_2$, —C(O)H, —$C(O)R^{3b}$, —$C(O)_2R^{3a}$, —$C(O)N(R^{3a})_2$, —$OC(O)N(R^{3a})_2$, —$N(R^{3a})C(O)_2R^{3a}$, —$N(R^{3a})C(O)N(R^{3a})_2$, —$OC(O)R^{3b}$, —$S(O)R^{3b}$, —$S(O)_2R^{3b}$, —$S(O)_2N(R^{3a})_2$, —$N(R^{3a})S(O)_2R^{3b}$, —$C(R^{3a})$=$N(R^{3a})$, and —$C(R^{3a})$=$N(OR^{3a})$, wherein said $C_{1-6}$alkyl, $C_{2-6}$alkenyl, $C_{2-6}$alkynyl, carbocyclyl, and heterocyclyl may be optionally substituted with one or more $R^{30}$;
$R^{3a}$ in each occurrence may be independently selected from H, $C_{1-6}$alkyl, carbocyclyl, and heterocyclyl, wherein said $C_{1-6}$alkyl, carbocyclyl, and heterocyclyl in each occurrence may be optionally and independently substituted with one or more $R^{30}$;
$R^{3b}$ in each occurrence may be independently selected from $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence may be optionally and independently substituted with one or more $R^{30}$;
$R^4$ may be selected from H, —CN, $C_{1-6}$alkyl, $C_{2-6}$alkenyl, $C_{2-6}$alkynyl, carbocyclyl, heterocyclyl, —$N(R^{4a})C(O)R^{4b}$, —N(R$^{4a}$)N(R$^{4a}$)$_2$, —NO$_2$, —C(O)H, —C(O)R$^{4b}$, —C(O)$_2$R$^{4a}$, —C(O)N(R$^{4a}$)$_2$, —OC(O)N(R$^{4a}$)$_2$, —N(R$^{4a}$)C(O)$_2$R$^{4a}$, —N(R$^{4a}$)C(O)N(R$^{4a}$)$_2$, —OC(O)R$^{4b}$, —S(O)R$^{4b}$, —S(O)$_2$R$^{4b}$, —S(O)$_2$N(R$^{4a}$)$_2$, —N(R$^{4a}$)S(O)$_2$R$^{4b}$, —C(R$^{4a}$)=N(R$^{4a}$), and —C(R$^{4a}$)=N(OR$^{4a}$), wherein said C$_{1-6}$alkyl, C$_{2-6}$alkenyl, C$_{2-6}$alkynyl, carbocyclyl, and heterocyclyl may be optionally substituted with one or more R$^{40}$;

R$^{4a}$ in each occurrence may be independently selected from H, C$_{1-6}$alkyl, carbocyclyl, and heterocyclyl, wherein said C$_{1-6}$alkyl, carbocyclyl, and heterocyclyl in each occurrence may be optionally and independently substituted with one or more R$^{40}$;

R$^{4b}$ in each occurrence may be independently selected from C$_{1-6}$alkyl, C$_{2-6}$alkenyl, C$_{2-6}$alkynyl, carbocyclyl, and heterocyclyl, wherein said C$_{1-6}$alkyl, C$_{2-6}$alkenyl, C$_{2-6}$alkynyl, carbocyclyl, and heterocyclyl in each occurrence may be optionally and independently substituted with one or more R$^{40}$;

R$^5$ may be independently selected from halo, —CN, C$_{1-6}$alkyl, C$_{2-6}$alkenyl, C$_{2-6}$alkynyl, carbocyclyl, heterocyclyl, —OR$^{5a}$, —SR$^{5a}$, —N(R$^{5a}$)$_2$, —N(R$^{5a}$)C(O)R$^{5b}$, —N(R$^{5a}$)N(R$^{5a}$)$_2$, —NO$_2$, —C(O)H, —C(O)R$^{5b}$, —C(O)$_2$R$^{5a}$, —C(O)N(R$^{5a}$)$_2$, —OC(O)N(R$^{5a}$)$_2$, —N(R$^{5a}$)C(O)$_2$R$^{5a}$, —N(R$^{6a}$)(O)N(R$^{5a}$)$_2$, —OC(O)R$^{5b}$, —S(O)R$^{5b}$, —S(O)$_2$R$^{5b}$, —S(O)$_2$N(R$^{5a}$)$_2$, —N(R$^{5a}$)S(O)$_2$R$^{5b}$, —C(R$^{5a}$)=N(R$^{5a}$), and —C(R$^{5a}$)=N(OR$^{5a}$);

R$^{5a}$ in each occurrence may be independently selected from H, C$_{1-6}$alkyl, carbocyclyl, and heterocyclyl;

R$^{5b}$ in each occurrence may be independently selected from C$_{1-6}$alkyl, C$_{2-6}$alkenyl, C$_{2-6}$alkynyl, carbocyclyl, and heterocyclyl;

R$^{10}$ in each occurrence may be independently selected from halo, —CN, C$_{1-6}$alkyl, C$_{2-6}$alkenyl, —N(R$^{10a}$)$_2$, —N—(R$^{10a}$)C(O)R$^{10b}$, C$_{2-6}$alkynyl, carbocyclyl, heterocyclyl, —OR$^{10a}$, —SR$^{10a}$, —N(R$^{10a}$)N(R$^{10a}$)$_2$, —NO$_2$, —C(O)H, —C(O)R$^{10b}$, —C(O)$_2$R$^{10a}$, —C(O)N(R$^{10a}$)$_2$, —OC(O)N(R$^{10a}$)$_2$, —N(R$^{10a}$)C(O)$_2$R$^{10a}$, —N(R$^{10a}$)C(O)N(R$^{10a}$)$_2$, —OC(O)R$^{10b}$, —S(O)R$^{10b}$, —S(O)$_2$R$^{10b}$, S(O)$_2$N(R$^{10a}$)$_2$, —N(R$^{10a}$)S(O)$_2$R$^{10b}$, —C(R$^{10a}$)N(R$^{10a}$), and —C(R$^{10a}$)=N(OR$^{10a}$);

R$^{10a}$ in each occurrence may be independently selected from H, C$_{1-6}$alkyl, carbocyclyl, and heterocyclyl;

R$^{10b}$ in each occurrence may be independently selected from C$_{1-6}$alkyl, C$_{2-6}$alkenyl, C$_{2-6}$alkynyl, carbocyclyl, and heterocyclyl;

R$^{20}$ in each occurrence may be independently selected from halo, —CN, C$_{1-6}$alkyl, C$_{2-6}$alkenyl, C$_{2-6}$alkynyl, carbocyclyl, heterocyclyl, —OR$^{20a}$, —SR$^{20a}$, —N(R$^{20a}$)$_2$, —N(R$^{20a}$)C(O)R$^{20b}$, —N(R$^{20a}$)N(R$^{20a}$)$_2$, —NO$_2$, —C(O)H, —C(O)R$^{20b}$, —C(O)$_2$R$^{20a}$, —C(O)N(R$^{20a}$)$_2$, —OC(O)N(R$^{20a}$)$_2$, —N(R$^{20a}$)C(O)$_2$R$^{20a}$, —N(R$^{20a}$)C(O)N(R$^{20a}$)$_2$, —OC(O)R$^{20b}$, —S(O)R$^{20b}$, —S(O)$_2$R$^{20b}$, —S(O)$_2$N(R$^{20a}$)$_2$, —N(R$^{20a}$)S(O)$_2$R$^{20b}$, —C(R$^{20a}$)=N(R$^{20a}$), and —C(R$^{20a}$)=N(OR$^{20a}$);

R$^{20a}$ in each occurrence may be independently selected from H, C$_{1-6}$alkyl, carbocyclyl, and heterocyclyl;

R$^{2b}$ in each occurrence may be independently selected from C$_{1-6}$alkyl, C$_{2-6}$alkenyl, C$_{2-6}$alkynyl, carbocyclyl, and heterocyclyl;

R$^{30}$ in each occurrence may be independently selected from halo, —CN, C$_{1-6}$alkyl, C$_{2-6}$alkenyl, C$_{2-6}$alkynyl, carbocyclyl, heterocyclyl, —OR$^{30a}$, —SR$^{30a}$, —N(R$^{30a}$)$_2$, —N(R$^{30a}$)C(O)R$^{30b}$, —N(R$^{30a}$)N(R$^{30a}$)$_2$, —NO$_2$, —C(O)H, —C(O)R$^{30b}$, —C(O)$_2$R$^{30a}$, —C(O)N(R$^{30a}$)$_2$, —OC(O)N(R$^{30a}$)$_2$, —N(R$^{30a}$)C(O)$_2$R$^{30a}$, —N(R$^{30a}$)C(O)N(R$^{30a}$)$_2$, —OC(O)R$^{30b}$, —S(O)R$^{30b}$, —S(O)$_2$R$^{30b}$, —S(O)$_2$N(R$^{30a}$)$_2$, —N(R$^{30a}$)S(O)$_2$R$^{30b}$, —C(R$^{30a}$)=N(R$^{30a}$), and —C(R$^{30a}$)=N(OR$^{30a}$);

R$^{30a}$ in each occurrence may be independently selected from H, C$_{1-6}$alkyl, carbocyclyl, and heterocyclyl;

R$^{30b}$ in each occurrence may be independently selected from C$_{1-6}$alkyl, C$_{2-6}$alkenyl, C$_{2-6}$alkynyl, carbocyclyl, and heterocyclyl;

R$^{40}$ in each occurrence may be independently selected from halo, —CN, C$_{1-6}$alkyl, C$_{2-6}$alkenyl, C$_{2-6}$alkynyl, carbocyclyl, heterocyclyl, —OR$^{40a}$, —SR$^{40a}$, —N(R$^{40a}$)$_2$, —N(R$^{40a}$)C(O)R$^{40b}$, —N(R$^{40a}$)N(R$^{40a}$)$_2$, —NO$_2$, —C(O)H, —C(O)R$^{40b}$, —C(O)$_2$R$^{40a}$, —C(O)N(R$^{40a}$)$_2$, —OC(O)N(R$^{40a}$)$_2$, —N(R$^{40a}$)C(O)$_2$R$^{40a}$, —N(R$^{40a}$)C(O)N(R$^{40a}$)$_2$, —OC(O)R$^{40b}$, —S(O)R$^{40b}$, —S(O)$_2$R$^{40b}$, —S(O)$_2$N(R$^{40a}$)$_2$, —N(R$^{40a}$)S(O)$_2$R$^{40b}$, —C(R$^{40a}$)=N(R$^{40a}$), and —C(R$^{40a}$)=N(OR$^{40a}$);

R$^{40a}$ in each occurrence may be independently selected from H, C$_{1-6}$alkyl, carbocyclyl, and heterocyclyl; and R$^{40b}$ in each occurrence may be independently selected from C$_{1-6}$alkyl, C$_{2-6}$alkenyl, C$_{2-6}$alkynyl, carbocyclyl, and heterocyclyl.

In this specification the prefix $C_{x-y}$ as used in terms such as $C_{x-y}$alkyl and the like (where x and y are integers) indicates the numerical range of carbon atoms that are present in the group; for example, $C_{1-4}$alkyl includes $C_1$alkyl(methyl), $C_2$alkyl(ethyl), $C_3$alkyl(propyl and isopropyl) and $C_4$alkyl (butyl, 1-methylpropyl, 2-methylpropyl, and t-butyl).

Alkyl—As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as 'isopropyl' are specific for the branched chain version only.

Alkenyl—As used herein, the term "alkenyl" refers to both straight and branched chain hydrocarbon radicals having the specified number of carbon atoms and containing at least one carbon-carbon double bond. For example, "$C_{2-6}$alkenyl" includes, but is not limited to, groups such as $C_{2-6}$alkenyl, $C_{2-4}$alkenyl, ethenyl, 2-propenyl, 2-methyl-2-propenyl, 3-butenyl, 4-pentenyl, and 5-hexenyl.

Alkynyl—As used herein, the term "alkynyl" refers to both straight and branched chain hydrocarbon radicals having the specified number of carbon atoms and containing at least one carbon-carbon triple bond. For example, "$C_{2-6}$alkynyl" includes, but is not limited to, groups such as $C_{2-6}$alkynyl, $C_{2-4}$alkynyl, ethynyl, 2-propynyl, 2-methyl-2-propynyl, 3-butynyl, 4-pentynyl, and 5-hexynyl.

Halo—As used herein, the term "halo" refers to fluoro, chloro, bromo and iodo. In one aspect, "halo" may be fluoro, chloro, and bromo. In another aspect, "halo" may be fluoro and chloro.

Carbocyclyl—As used herein, the term "carbocyclyl" refers to a saturated, partially saturated, or unsaturated, mono or bicyclic carbon ring that contains 3 to 12 ring atoms, of which one or more —CH$_2$— groups may be optionally replaced with a corresponding number of —C(O)— groups. Illustrative examples of "carbocyclyl" include, but are not limited to, adamantyl, cyclopropyl, cyclobutyl, cyclopentyl, cyclopentenyl, cyclohexyl, cyclohexenyl, indanyl, naphthyl, oxocyclopentyl, 1-oxoindanyl, phenyl, and tetralinyl. In one aspect, "carbocyclyl" may be cyclopropyl.

3- to 5-Membered Carbocyclyl—In one aspect, "carbocyclyl" may be "3- to 5-membered carbocyclyl." The term "3- to 5-membered carbocyclyl" refers to a saturated or partially saturated monocyclic carbon ring containing 3 to 5 ring atoms, of which one or more —CH$_2$-groups may be optionally replaced with a corresponding number of —C(O)— groups. Illustrative examples of "3- to 5-membered carbocyclyl" include cyclopropyl, cyclobutyl, cyclopentyl, oxocyclopentyl, and cyclopentenyl. In one aspect, "3- to 5-membered carbocyclyl" may be cyclopropyl.

Heterocyclyl—As used herein, the term "heterocyclyl" refers to a saturated, partially saturated, or unsaturated, mono or bicyclic ring containing 4 to 12 ring atoms of which at least one ring atom is selected from nitrogen, sulfur, and oxygen, and which may, unless otherwise specified, be carbon or nitrogen linked, and of which a —CH$_2$— group can optionally be replaced by a —C(O)—. Ring sulfur atoms may be optionally oxidized to form S-oxides. Ring nitrogen atoms may be optionally oxidized to form N-oxides. Illustrative examples of the term "heterocyclyl" include, but are not limited to, 1,3-benzodioxolyl, 3,5-dioxopiperidinyl, furanyl, imidazolyl, indolyl, isoquinolinyl, isothiazolyl, isoxazolyl, morpholino, 2-oxa-5-azabicyclo[2.2.1]hept-5-yl, oxazolyl, 2-oxopyrrolidinyl, 2-oxo-1,3-thiazolidinyl, piperazinyl, piperidyl, 2H-pyranyl, pyrazolyl, pyridinyl, pyrrolyl, pyrrolidinyl, pyrrolidinyl, pyrimidinyl, pyrazinyl, pyrazolyl, pyridazinyl, 4-pyridonyl, quinolyl, tetrahydrofuranyl, tetrahydropyranyl, thiazolyl, thiadiazolyl, thiazolidinyl, thiomorpholino, thiophenyl, pyridinyl-N-oxidyl and quinolinyl-N-oxidyl.

5- or 6-Membered Heterocyclyl—In another aspect, "heterocyclyl" may be "5- or 6-membered heterocyclyl," which refers to a saturated, partially saturated, or unsaturated, monocyclic ring containing 5 or 6 ring atoms, of which at least one ring atom is selected from nitrogen, sulfur, and oxygen, and of which a —CH$_2$— group may be optionally replaced by a —C(O)— group. Unless otherwise specified, "5- or 6-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "5- or 6-membered heterocyclyl" include, but are not limited to, 3,5-dioxopiperidinyl, furanyl, imidazolyl, isothiazolyl, isoxazolyl, morpholino, oxazolyl, 2-oxopyrrolidinyl, 2-oxo-1,3-thiazolidinyl, piperazinyl, piperidyl, 2H-pyranyl, pyrazolyl, pyridinyl, pyrrolyl, pyrrolidinyl, pyrrolidinyl, pyrimidinyl, pyrazinyl, pyrazolyl, pyridazinyl, 4-pyridonyl, tetrahydrofuranyl, tetrahydropyranyl, thiazolyl, thiadiazolyl, thiazolidinyl, thiomorpholino, thiophenyl, pyridine-N-oxidyl.

6-Membered Heterocyclyl—In still another aspect, "heterocyclyl" and "5- or 6-membered heterocyclyl" may be "6-membered heterocyclyl," which refers to a saturated, partially saturated, or unsaturated, monocyclic ring containing 6 ring atoms, of which at least one ring atom is selected from nitrogen, sulfur, and oxygen, and of which a —CH$_2$— group may be optionally replaced by a —C(O)— group. Unless otherwise specified, "6-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "6-membered heterocyclyl" include, but are not limited to, 3,5-dioxopiperidinyl, morpholino, piperazinyl, piperidinyl, 2H-pyranyl, pyrazinyl, pyridazinyl, pyridinyl, and pyrimidinyl.

5-Membered Heterocyclyl—In a further aspect, "heterocyclyl" and "5- or 6-membered heterocyclyl" may be "5-membered heterocyclyl," which refers to a saturated, partially saturated, or unsaturated, monocyclic ring containing 5 ring atoms, of which at least one ring atom is selected from nitrogen, sulfur, and oxygen, and of which a —CH$_2$— group may be optionally replaced by a —C(O)— group. Unless otherwise specified, "5-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "5-membered heterocyclyl" include, but are not limited to, furanyl, imidazolyl, isothiazolyl, isoxazolyl, oxazolyl, pyrazolyl, pyrrolyl, pyrrolidinyl, tetrahydrofuranyl, thiazolyl, and thiophenyl.

Where a particular R group (e.g. $R^{1a}$, $R^{10}$, etc.) is present in a compound of Formula (I) more than once, it is intended that each selection for that R group is independent at each occurrence of any selection at any other occurrence. For example, the —N(R)$_2$ group is intended to encompass: 1) those —N(R)$_2$ groups in which both R substituents are the same, such as those in which both R substituents are, for example, $C_{1-6}$alkyl; and 2) those —N(R)$_2$ groups in which each R substituent is different, such as those in which one R substituent is, for example, H, and the other R substituent is, for example, carbocyclyl.

Unless specifically stated, the bonding atom of a group may be any suitable atom of that group; for example, propyl includes prop-1-yl and prop-2-yl.

Effective Amount—As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

In particular, an effective amount of a compound of Formula (I) for use in the treatment of cancer is an amount sufficient to symptomatically relieve in a warm-blooded animal such as man, the symptoms of cancer and myeloproliferative diseases, to slow the progression of cancer and myeloproliferative diseases, or to reduce in patients with symptoms of cancer and myeloproliferative diseases the risk of getting worse.

Leaving Group—As used herein, the phrase "leaving group" is intended to refer to groups readily displaceable by a nucleophile such as an amine nucleophile, and alcohol nucleophile, or a thiol nucleophile. Examples of suitable leaving groups include halo, such as chloro and bromo; and sulfonyloxy groups, such as methanesulfonyloxy and toluene-4-sulfonyloxy.

Optionally substituted—As used herein, the phrase "optionally substituted," indicates that substitution is optional and therefore it is possible for the designated group to be either substituted or unsubstituted. In the event a substitution is desired, any number of hydrogens on the designated group may be replaced with a selection from the indicated substituents, provided that the normal valency of the atoms on a particular substituent is not exceeded, and that the substitution results in a stable compound.

One or More—In one aspect, when a particular group is designated as being optionally substituted with "one or more" substituents, the particular may be unsubstituted. In another aspect, the particular group may bear one substituent. In another aspect, the particular substituent may bear two substituents. In still another aspect, the particular group may bear three substituents. In yet another aspect, the particular group may bear four substituents. In a further aspect, the particular group may bear one or two substituents. In still a further aspect, the particular group may be unsubstituted, or may bear one or two substituents.

Pharmaceutically Acceptable—As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Protecting Group—As used herein, the term "protecting group" is intended to refer to those groups used to prevent selected reactive groups (such as carboxy, amino, hydroxy, and mercapto groups) from undergoing undesired reactions.

Illustrative examples of suitable protecting groups for a hydroxy group include, but are not limited to, an acyl group; alkanoyl groups such as acetyl; aroyl groups, such as benzoyl; silyl groups, such as trimethylsilyl; and arylmethyl groups, such as benzyl. The deprotection conditions for the above hydroxy protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

Illustrative examples of suitable protecting groups for an amino group include, but are not limited to, acyl groups; alkanoyl groups such as acetyl; alkoxycarbonyl groups, such as methoxycarbonyl, ethoxycarbonyl, and t-butoxycarbonyl; arylmethoxycarbonyl groups, such as benzyloxycarbonyl; and aroyl groups, such benzoyl. The deprotection conditions for the above amino protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric, phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid, for example boron trichloride). A suitable alternative protecting group for a primary amino group is, for example, a phthaloyl group, which may be removed by treatment with an alkylamine, for example dimethylaminopropylamine or 2-hydroxyethylamine, or with hydrazine. Another suitable protecting group for an amine is, for example, a cyclic ether such as tetrahydrofuran, which may be removed by treatment with a suitable acid such as trifluoroacetic acid.

The protecting groups may be removed at any convenient stage in the synthesis using conventional techniques well known in the chemical art, or they may be removed during a later reaction step or work-up.

With reference to substituent $R^1$ for illustrative purposes, the following substituent definitions have the indicated meanings.

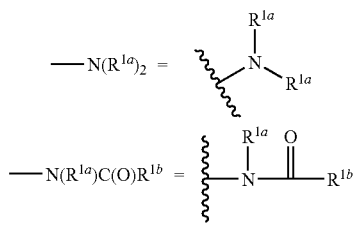

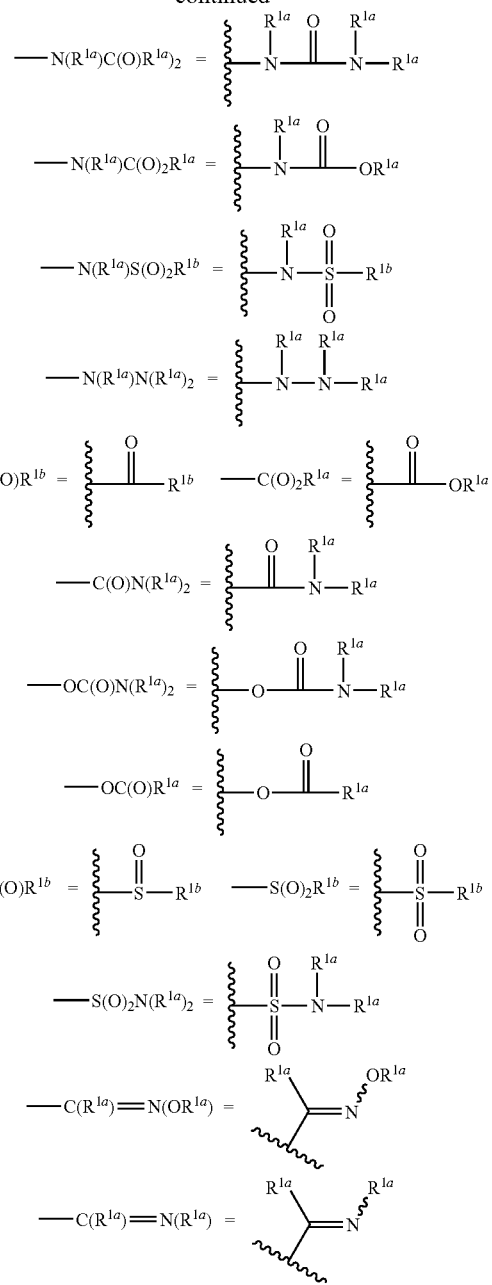

The compounds discussed herein in many instances were named and/or checked with ACD/Name by ACD/Labs®.

Compounds of Formula (I) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethyl-sulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others.

Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Some compounds of Formula (I) may have chiral centres and/or geometric isomeric centres (E- and Z-isomers), and it is to be understood that the invention encompasses all such optical, diastereoisomers and geometric isomers. The invention further relates to any and all tautomeric forms of the compounds of Formula (I).

It is also to be understood that certain compounds of Formula (I) can exist in solvated as well as unsolvated forms such as, for example, hydrated forms. It is to be understood that the invention encompasses all such solvated forms.

Additional embodiments of the invention are as follows. These additional embodiments relate to compounds of Formula (I) and pharmaceutically acceptable salts thereof. Such specific substituents may be used, where appropriate, with any of the definitions, claims or embodiments defined hereinbefore or hereinafter.

Q

In one aspect, Q may be selected from N and $C(R^3)$; and $R^3$ may be selected from H and halo.

In another aspect, Q may be N.

In still another aspect, Q may be $C(R^3)$; and $R^3$ may be selected from H and halo.

In still another aspect, Q may be $C(R^3)$; and $R^3$ may be halo.

In still another aspect, Q may be $C(R^3)$; and $R^3$ may be selected from H, fluoro, and chloro.

In still another aspect, Q may be $C(R^3)$; and $R^3$ may be H.

In still another aspect, Q may be $C(R^3)$; and $R^3$ may be fluoro.

In yet another aspect, Q may be $C(R^3)$; and $R^3$ may be chloro.

D

In one aspect, D may be selected from N.

In another aspect, D may be selected from CH.

$R^1$ $R^1$ may be selected from H, —CN, $C_{1-6}$alkyl, $C_{2-6}$alkenyl, $C_{2-6}$alkynyl, 3- to 5-membered carbocyclyl, 5-membered heterocyclyl, —$OR^{1a}$, —$SR^{1a}$, —$N(R^{1a})_2$, —$N(R^{1a})C(O)R^{1b}$, —$N(R^{1a})N(R^{1a})_2$, —$NO_2$, —C(O)H, —$C(O)R^{1b}$, —$C(O)_2R^{1a}$, —$C(O)N(R^{1a})_2$, —$OC(O)N(R^{1a})_2$, —$N(R^{1a})C(O)_2R^{1a}$, —$N(R^{1a})C(O)N(R^{1a})_2$, —$OC(O)R^{1b}$, —$S(O)R^{1b}$, —$S(O)_2R^{1b}$, —$S(O)_2N(R^{1a})_2$, —$N(R^{1a})S(O)_2R^{1b}$, —$C(R^{1a})$=N$(R^{1a})$, and —$C(R^{1a})$=$N(OR^{1a})$;

$R^{1a}$ in each occurrence may be independently selected from H, $C_{1-6}$alkyl, 3- to 5-membered carbocyclyl, and 5-membered heterocyclyl;

$R^{1b}$ in each occurrence may be independently selected from $C_{1-6}$alkyl, $C_{2-6}$alkenyl, $C_{2-6}$alkynyl, 3- to 5-membered carbocyclyl, and 5-membered heterocyclyl.

In one aspect, $R^1$ may be selected from $C_{1-6}$alkyl, 3- to 5-membered carbocyclyl, and —$OR^{1a}$; and $R^{1a}$ may be $C_{1-6}$alkyl.

In another aspect, $R^1$ may be $C_{1-6}$alkyl.

In still another aspect, $R^1$ may be 3- to 5-membered carbocyclyl.

In yet another aspect, $R^1$ may be —$OR^{1a}$; and $R^{1a}$ may be $C_{1-6}$alkyl.

In a further aspect, $R^1$ may be selected from methyl, cyclopropyl, isopropoxy, and ethoxy.

In still a further aspect, $R^1$ may be methyl.

In yet a further aspect, $R^1$ may be cyclopropyl.

In one aspect, $R^1$ may be isopropoxy.

In another aspect, $R^1$ may be ethoxy.

$R^2$

In one aspect, $R^2$ may be selected from H, halo, —CN, $C_{1-6}$alkyl, $C_{2-6}$alkenyl, $C_{2-6}$alkynyl, carbocyclyl, heterocyclyl, —$OR^{2a}$, —$SR^{2a}$, —$N(R^{2a})_2$, —$N(R^{2a})C(O)R^{2b}$, —$N(R^{2a})N(R^{2a})_2$, —$NO_2$, —C(O)H, —$C(O)R^{2b}$, —$C(O)_2R^{2a}$, —$C(O)N(R^{2a})_2$, —$OC(O)N(R^{2a})_2$, —$N(R^{2a})C(O)_2R^{2a}$, —$N(R^{2a})C(O)N(R^{2a})_2$, —$OC(O)R^{2b}$, —$S(O)R^{2b}$, —$S(O)_2R^{2b}$, —$S(O)_2N(R^{2a})_2$, —$N(R^{2a})S(O)_2R^{2b}$, —$C(R^{2a})$=N$(R^{2a})$, and —$C(R^{2a})$=$N(OR^{2a})$;

$R^{2a}$ in each occurrence may be independently selected from H, $C_{1-6}$alkyl, carbocyclyl, and heterocyclyl; and $R^{2b}$ in each occurrence may be independently selected from $C_{1-6}$alkyl, $C_{2-6}$alkenyl, $C_{2-6}$alkynyl, carbocyclyl, and heterocyclyl.

In one aspect, $R^2$ may be selected from H, heterocyclyl, —$OR^{2a}$, —$N(R^{2a})_2$, —$C(O)R^{2b}$;

$R^{2a}$ in each occurrence may be independently selected from H, $C_{1-6}$alkyl, and heterocyclyl; and $R^{2b}$ may be heterocyclyl.

In one aspect, $R^2$ may be H.

In another aspect, $R^2$ may be heterocyclyl.

In yet another aspect, $R^2$ may be —$OR^{2a}$; and $R^{2a}$ may be selected from $C_{1-6}$alkyl.

In yet another aspect, $R^2$ may be —$N(R^{2a})_2$; and $R^{2a}$ in each occurrence may be independently selected from H and heterocyclyl.

In still another aspect, $R^2$ may be —$C(O)R^{2b}$; and $R^{21}$ be heterocyclyl.

In yet another aspect, $R^2$ may be selected from H, methoxy, morpholin-4-yl, 2-morpholin-4-yl-2-oxoethyl, and tetrahydro-2H-pyran-4-ylamino.

In a further aspect, $R^2$ may be methoxy.

In still a further aspect, $R^2$ may be morpholin-4-yl.

In yet a further aspect, $R^2$ may be 2-morpholin-4-yl-2-oxoethyl.

In one aspect, $R^2$ may be tetrahydro-2H-pyran-4-ylamino $R^4$

In one aspect, $R^4$ may be selected from $C_{1-6}$alkyl, $C_{2-6}$alkenyl, $C_{2-6}$alkynyl, wherein said $C_{1-6}$alkyl, $C_{2-6}$alkenyl, $C_{2-6}$alkynyl may be optionally substituted with one or more $R^{40}$;

$R^{40}$ in each occurrence may be independently selected from halo, —CN, $C_{1-6}$alkyl, $C_{2-6}$alkenyl, $C_{2-6}$alkynyl, carbocyclyl, heterocyclyl, a —$SR^{40a}$, —$SR^{40a}$, —$N(R^{40a})_2$, —$N(R^{40a})C(O)R^{40b}$, —$N(R^{40a})N(R^{40a})_2$, —$NO_2$, —C(O)H, —C(O)

$R^{40b}$, —$C(O)_2R^{40a}$, —$C(O)N(R^{40a})_2$, —$OC(O)N(R^{40a})_2$, —$N(R^{40a})C(O)_2R^{40a}$, —$N(R^{40a})C(O)N(R^{40a})_2$, —$OC(O)R^{40b}$, —$S(O)R^{40b}$, —$S(O)_2R^{40b}$, —$S(O)_2N(R^{40a})_2$, —$N(R^{40a})S(O)_2R^{40b}$, —$C(R^{40a})=N(R^{40a})$, and —$C(R^{40a})=N(OR^{40a})$;

$R^{40a}$ in each occurrence may be independently selected from H, $C_{1-6}$alkyl, carbocyclyl, and heterocyclyl; and $R^{40b}$ in each occurrence may be independently selected from $C_{1-6}$alkyl, $C_{2-6}$alkenyl, $C_{2-6}$alkynyl, carbocyclyl, and heterocyclyl.

In one aspect, $R^4$ may be selected from $C_{1-6}$alkyl, wherein said $C_{1-6}$alkyl may be optionally substituted with one or more $R^{40}$;

$R^{40}$ may be —$OR^{40a}$; and $R^{40a}$ may be H.

In another aspect, $R^4$ may be selected from methyl, ethyl, and hydroxymethyl.

In still another aspect, $R^4$ may be methyl.

In yet another aspect, $R^4$ may be ethyl.

In one aspect, $R^4$ may be hydroxymethyl.
$R^5$

In one aspect, $R^5$ may be halo.

In another aspect, $R^5$ may be fluoro.

Q, D, $R^1$, $R^2$, $R^4$, and $R^5$

In one aspect, Q may be selected from N and $C(R^3)$;

D may be selected from N and CH;

$R^2$ may be selected from H, halo, —CN, $C_{1-6}$alkyl, $C_{2-6}$alkenyl, $C_{2-6}$alkynyl, carbocyclyl, heterocyclyl, —$OR^{2a}$, —$SR^{2a}$, —$N(R^{2a})_2$, —$N(R^{2a})C(O)R^{2b}$, —$N(R^{2a})N(R^{2a})_2$, —$NO_2$, —$C(O)H$, —$C(O)R^{2b}$, —$C(O)_2R^{2a}$, —$C(O)N(R^{2a})_2$, —$OC(O)N(R^{2a})_2$, —$N(R^{2a})C(O)_2R^{2a}$, —$N(R^{2a})C(O)N(R^{2a})_2$, —$OC(O)R^{2b}$, —$S(O)R^{2b}$, —$S(O)_2R^{2b}$, —$S(O)_2N(R^{2a})_2$, —$N(R^{2a})S(O)_2R^{2b}$, —$C(R^{2a})=N(R^{2a})$, and —$C(R^{2a})=N(OR^{2a})$;

$R^{2a}$ in each occurrence may be independently selected from H, $C_{1-6}$alkyl, carbocyclyl, and heterocyclyl;

$R^{2b}$ each occurrence may be independently selected from $C_{1-6}$alkyl, $C_{2-6}$alkenyl, $C_{2-6}$alkynyl, carbocyclyl, and heterocyclyl;

$R^3$ may be selected from H and halo;

$R^4$ may be selected from $C_{1-6}$alkyl, $C_{2-6}$alkenyl, $C_{2-6}$alkynyl, wherein said $C_{1-6}$alkyl, $C_{2-6}$alkenyl, $C_{2-6}$alkynyl may be optionally substituted with one or more $R^{40}$;

$R^{40}$ in each occurrence may be independently selected from halo, —CN, $C_{1-6}$alkyl, $C_{2-6}$alkenyl, $C_{2-6}$alkynyl, carbocyclyl, heterocyclyl, —$OR^{40a}$, —$SR^{40a}$, —$N(R^{40a})_2$, —$N(R^{40a})C(O)R^{40b}$, —$N(R^{40a})N(R^{40a})_2$, —$NO_2$, —$C(O)H$, —$C(O)R^{40b}$, —$C(O)_2R^{40a}$, —$C(O)N(R^{40a})_2$, —$OC(O)N(R^{40a})_2$, —$N(R^{40a})C(O)_2R^{40a}$, —$N(R^{40a})C(O)N(R^{40a})_2$, $OC(O)R^{40b}$, —$S(O)R^{40b}$, —$S(O)_2R^{40b}$, —$S(O)_2N(R^{40a})_2$, —$N(R^{40a})S(O)_2R^{40b}$, —$C(R^{40a})N(R^{40a})=N(OR^{40a})$, and —$C(R^{40a})$;

$R^{40a}$ in each occurrence may be independently selected from H, $C_{1-6}$alkyl, carbocyclyl, and heterocyclyl;

$R^{40b}$ in each occurrence may be independently selected from $C_{1-6}$alkyl, $C_{2-6}$alkenyl, $C_{2-6}$alkynyl, carbocyclyl, and heterocyclyl; and $R^5$ may be halo.

In another aspect, Q may be selected from N and $C(R^3)$;

D may be selected from N and CH;

$R^1$ may be selected from $C_{1-6}$alkyl, 3- to 5-membered carbocyclyl, and —$OR^{1a}$;

$R^{1a}$ may be $C_{1-6}$alkyl;

$R^2$ may be selected from H, heterocyclyl, —$OR^{2a}$, —$N(R^{2a})_2$, —$C(O)R^{2b}$;

$R^{2a}$ in each occurrence may be independently selected from H, $C_{1-6}$alkyl, and heterocyclyl;

$R^{2b}$ be heterocyclyl;

$R^3$ may be selected from H and halo;

$R^4$ may be $C_{1-6}$alkyl, wherein said $C_{1-6}$alkyl may be optionally substituted with one or more $R^{40}$;

$R^5$ may be halo;

$R^{40}$ may be —$OR^{40a}$; and $R^{40a}$ may be H.

In still another aspect, Q may be selected from N and $C(R^3)$;

D may be selected from N and CH;

$R^1$ may be selected from methyl, cyclopropyl, isopropoxy, and ethoxy;

$R^2$ may be selected from H, methoxy, morpholin-4-yl, 2-morpholin-4-yl-2-oxoethyl, and tetrahydro-2H-pyran-4-ylamino;

$R^3$ may be selected from H, fluoro, and chloro;

$R^4$ may be selected from methyl, ethyl, and hydroxymethyl; and $R^5$ may be fluoro.

In yet another aspect the compound of Formula (I) may be a compound of Formula (Ia):

Formula (Ia)

or a pharmaceutically acceptable salt thereof, wherein Q, D, $R^1$, $R^2$, $R^4$, and $R^5$ are as defined hereinabove.

In one aspect of the present invention, there is provided a compound of Formula (I), or a pharmaceutically acceptable salt thereof, as illustrated by the Examples, each of which provides a further independent aspect of the invention.

Utility

JAK2

The compounds of Formula (I) have utility for the treatment of myeloproliferative disorders, myelodysplastic syndrome and cancer by inhibiting the tyrosine kinases, particularly the JAK family and more particularly JAK2. Methods of treatment target tyrosine kinase activity, particularly the JAK family activity and more particularly JAK2 activity, which is involved in a variety of myeloproliferative disorders, myelodysplastic syndrome and cancer related processes. Thus, inhibitors of tyrosine kinase, particularly the JAK family and more particularly JAK2, are expected to be active against myeloproliferative disorders such as chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and neoplastic disease such as carcinoma of the breast, ovary, lung, colon, prostate or other tissues, as well as leukemias, myelomas and lymphomas, tumors of the central and peripheral nervous system, and other tumor types such as melanoma, fibrosarcoma and osteosarcoma. Tyrosine kinase inhibitors, particularly the JAK family inhibitors and more particularly JAK2 inhibitors are also expected to be useful for the treatment other proliferative diseases including but not limited to autoimmune, inflammatory, neurological, and cardiovascular diseases.

The compounds of Formula (I) have been shown to inhibit tyrosine kinases, particularly the JAK family and more particularly JAK2, as determined by the JAK2 Assay described herein.

The compounds of Formula (I) should also be useful as standards and reagents in determining the ability of a potential pharmaceutical to inhibit tyrosine kinases, particularly the JAK family and more particularly JAK2. These would be provided in commercial kits comprising a compound of this invention.

JAK2 kinase activity was determined by measuring the kinase's ability to phosphorylate synthetic tyrosine residues within a generic polypeptide substrate using an Amplified Luminescent Proximity Assay (Alphascreen) technology (PerkinElmer, 549 Albany Street, Boston, Mass.).

To measure JAK2 kinase activity, a commercially available purified enzyme may be used. The enzyme may be a C-terminal His6-tagged, recombinant, human JAK2, amino acids 808-end, (Genbank Accession number NM 004972) expressed by baculovirus in Sf21 cells (Upstate Biotechnology MA). After incubation of the kinase with a biotinylated substrate and adenosine triphosphate (ATP) for 60 minutes at room temperature, the kinase reaction may be stopped by the addition of 30 mM ethylenediaminetetraacetic acid (EDTA). The reaction may be performed in 384 well microtitre plates and the reaction products may be detected with the addition of streptavidin coated Donor Beads and phosphotyrosine-specific antibodies coated Acceptor Beads using the EnVision Multilabel Plate Reader after an overnight incubation at room temperature.

the Trks and more particularly Trk A and B. Methods of treatment target tyrosine kinase activity, particularly the Trk activity and more particularly Trk A and B activity, which is involved in a variety of cancer related processes. Thus, inhibitors of tyrosine kinase, particularly the Trks and more particularly Trk A and B, are expected to be active against neoplastic disease such as carcinoma of the breast, ovary, lung, colon, prostate or other tissues, as well as leukemias and lymphomas, tumors of the central and peripheral nervous system, and other tumor types such as melanoma, fibrosarcoma and osteosarcoma. Tyrosine kinase inhibitors, particularly the Trk inhibitors and more particularly Trk A and B inhibitors are also expected to be useful for the treatment other proliferative diseases including but not limited to autoimmune, inflammatory, neurological, and cardiovascular diseases.

In addition, the compounds of the invention are expected to be of value in the treatment or prophylaxis of cancers selected with up regulated of constitutively activated Trk kinases, including but not limited to, oncogenic rearrangements leading to ETV6-TrkC fusions, TRP-TrkA fusions proteins, AML-ETO (t8; 21), autocrine or paracrine signalling leading to elevated serum levels of NGF, BDNF, neurotropins or tumors with constitutively active Trk associated with disease aggressiveness, tumor growth and proliferation or survival signalling.

Compounds of the present invention have been shown to inhibit tyrosine kinases, particularly the Trks and more particularly Trk A and B, as determined by the Trk A Assay described herein. Compounds provided by this invention should also be useful as standards and reagents in determining the ability of a potential pharmaceutical to inhibit tyrosine kinases, particularly the Trks and more particularly Trk A and B. These would be provided in commercial kits comprising a compound of this invention.

| | |
|---|---|
| Peptide substrate | TYK2 (Tyr 1054/1055 biotinylated peptide) Cell Signalling Technology #2200B. 402 µM stock. |
| ATP Km | 15 µM |
| Assay conditions | 150 pM JAK2 enzyme, 15 µM ATP, 80 nM Tyk2, 10 mM MgCl$_2$, 50 mM Hepes buffer pH 7.5, 1 mM DTT, 0.025% DTT. |
| Incubation | 60 minutes, room temperature |
| Termination/Detection conditions | 6.3 mM HEPES, 30 mM EDTA, 525 µg/ml BSA, 40 mM NaCl, 0.007% Triton ® X-100, 12 ng/ml of Donor Beads, 12 ng/ml of Acceptor Beads |
| Detection incubation | overnight, room temperature |
| Fluometer settings | Excitation = 680 nm Emission = 570 nm Excitation Time = 180 ms Total Measurement Time = 550 ms |

Although the pharmacological properties of the compounds of Formula (I) vary with structural change, it is believed that in general, activity possessed by compounds of Formula (I) may be demonstrated at IC$_{50}$ concentrations (concentrations to achieve 50% inhibition) or doses at a level below 10 µM.

When tested in the above in-vitro assay the JAK inhibitory activity of the following example was measured at the following IC$_{50}$.

| Ex | IC$_{50}$ (µM) |
|---|---|
| 17 | 0.003 |

TRK

The compounds of Formula (I) have utility for the treatment of cancer by inhibiting the tyrosine kinases, particularly Trk A kinase activity was determined by measuring the kinase's ability to phosphorylate synthetic tyrosine residues within a generic polypeptide substrate using an Amplified Luminescent Proximity Assay (Alphascreen) technology (PerkinElmer, 549 Albany Street, Boston, Mass.).

To measure Trk A kinase activity, the intracellular domain of a HIS-tagged human Trk A kinase (amino acids 442-796 of Trk A, Swiss-Prot Primary Accession Number P04629) may be expressed in SF9 cells and purified using standard nickel column chromatography. After incubation of the kinase with a biotinylated substrate and adenosine triphosphate (ATP) for 20 minutes at room temperature, the kinase reaction may be stopped by the addition of 30 mM ethylenediaminetetraacetic acid (EDTA). The reaction may be performed in 384 well microtitre plates and the reaction products may be detected with the addition of strepavidin coated Donor Beads and phosphotyrosine-specific antibodies coated Acceptor Beads using the EnVision Multilabel Plate Reader after an overnight incubation at room temperature.

| | |
|---|---|
| Peptide substrate | PolyEY-biotin (PGT-bio.) |
| ATP Km | 70 μM |
| Assay conditions | 0.838 ng/ml Trk A, 9 mM HEPES, 45 μg/ml BSA, 10 mM MnCl$_2$, 5 nM PGT-bio, 0.01% Triton ® X-100, 70 μM ATP |
| Incubation | 20 minutes, room temperature |
| Termination/Detection conditions | 6.3 mM HEPES, 30 mM EDTA, 525 μg/ml BSA, 40 mM NaCl, 0.007% Triton ® X-100, 12 ng/ml of Donor Beads, 12 ng/ml of Acceptor Beads |
| Detection incubation | overnight, room temperature |
| Fluometer settings | Excitation = 680 nm Emission = 570 nm Excitation Time = 180 ms Total Measurement Time = 550 ms |

Although the pharmacological properties of the compounds of Formula (I) vary with structural change, it is believed that in general, activity possessed by compounds of Formula (I), or pharmaceutically acceptable salts thereof, may be demonstrated at IC$_{50}$ concentrations (concentrations to achieve 50% inhibition) or doses at a level below 10 μM.

When tested in an assay based on the in-vivo assay described above, the Trk inhibitory activity of the following examples were measured at the following IC$_{50}$s.

| Ex | IC$_{50}$ (μM) |
|---|---|
| 1 | 0.003 |
| 2 | 0.003 |
| 3 | 0.003 |
| 4 | 0.012 |
| 5 | 0.005 |
| 6 | 0.003 |
| 7 | 0.003 |
| 8 | 0.003 |
| 9 | 0.003 |
| 10 | 0.003 |
| 11 | 0.003 |
| 12 | 0.003 |
| 13 | 0.006 |
| 14 | 0.004 |
| 15 | 3.809 |
| 16 | 0.061 |
| 17 | 0.014 |
| 18 | 0.311 |
| 19 | 7.250 |
| 20 | 0.475 |
| 21 | 0.096 |
| 22 | 0.773 |
| 23 | 0.003 |

Thus, in one aspect, there is provided a compound of Formula (I), or a pharmaceutically acceptable salt thereof, for use as a medicament.

In another aspect, there is provided the use of a compound of Formula (I), or a pharmaceutically acceptable salt thereof, in the manufacture of a medicament for the treatment or prophylaxis of myeloproliferative disorders, myelodysplastic syndrome, and cancer, in a warm-blooded animal such as man.

In still another aspect, there is provided the use of a compound of Formula (I), or a pharmaceutically acceptable salt thereof, in the manufacture of a medicament for the treatment or prophylaxis of myeloproliferative disorders, myelodysplastic syndrome and cancers (solid and hematologic tumors), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acromegaly, acute and chronic inflammation, bone diseases, and ocular diseases with retinal vessel proliferation, in a warm-blooded animal such as man.

In yet another aspect, there is provided the use of a compound of Formula (I), or a pharmaceutically acceptable salt thereof, in the manufacture of a medicament for treating chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and cancers selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma and leukaemia, in a warm-blooded animal such as man.

In a further aspect, there is provided the use of a compound of Formula (I), or a pharmaceutically acceptable salt thereof, in the manufacture of a medicament for treating inflammatory disorders, including such conditions as: allergies, including allergic rhinitis/sinusitis, skin allergies (urticaria/hives, angioedema, atopic dermatitis), food allergies, drug allergies, insect allergies, and rare allergic disorders such as mastocytosis; asthma; Arthritis, including osteoarthritis, rheumatoid arthritis, and spondyloarthropathies; Autoimmune conditions, including systemic lupus erythematosus, dermatomyositis, polymyositis, inflammatory neuropathies (Guillain Barré, inflammatory polyneuropathies), Crohn's disease, ulcerative colitis, vasculitis (Wegener's granulomatosus, polyarteritis nodosa), and rare disorders such as polymyalgia rheumatica, temporal arteritis, Sjogren's syndrome, Bechet's disease, Churg-Strauss syndrome, and Takayasu's arteritis; cardiovascular inflammation; gastrointestinal inflammation; infection and immunity; leukocyte biology and immunology; neuroinflammatory disorders; and transplantation.

In a further aspect, there is provided the use of a compound of Formula (I), or a pharmaceutically acceptable salt thereof, in the manufacture of a medicament for treating persistent pain states, including neuropathic pain, and pain associated with inflammation.

In a further aspect, there is provided the use of a compound of Formula (I), or a pharmaceutically acceptable salt thereof, in the manufacture of a medicament for the production of an anti-proliferative effect, in a warm-blooded animal such as man.

In still a further aspect, there is provided the use of a compound of Formula (I), or a pharmaceutically acceptable salt thereof, in the manufacture of a medicament for the production of a JAK inhibitory effect.

In yet a further a further aspect, there is provided the use of a compound of Formula (I), or a pharmaceutically acceptable salt thereof, in the manufacture of a medicament for the production of a TRK inhibitory effect.

In one aspect, there is provided the use of a compound of Formula (I), or a pharmaceutically acceptable salt thereof, in the manufacture of a medicament for the treatment of cancer.

In another aspect, there is provided a method of treating myeloproliferative disorders, myelodysplastic syndrome, and cancer, in a warm-blooded animal such as man, said method comprising administering to said animal an effective amount of a compound of Formula (I), or a pharmaceutically acceptable salt thereof.

In still another aspect, there is provided a method of treating myeloproliferative disorders, myelodysplastic syndrome, and cancers (solid and hematologic tumors), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acromegaly, acute and chronic inflammation, bone diseases, and ocular diseases with retinal vessel proliferation, in a warm-blooded animal such as man, said method comprising administering to said animal an effective amount of a compound of Formula (I), or a pharmaceutically acceptable salt thereof.

In yet another aspect, there is provided a method of treating chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and cancers selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma and leukaemia, in a warm-blooded animal such as man, said method comprising administering to said animal an effective amount of compound of Formula (I), or a pharmaceutically acceptable salt thereof.

In a further aspect, there is provided the a method of treating inflammatory disorders, including such conditions as: allergies, including allergic rhinitis/sinusitis, skin allergies (urticaria/hives, angioedema, atopic dermatitis), food allergies, drug allergies, insect allergies, and rare allergic disorders such as mastocytosis; asthma; Arthritis, including osteoarthritis, rheumatoid arthritis, and spondyloarthropathies; Autoimmune conditions, including systemic lupus erythematosus, dermatomyositis, polymyositis, inflammatory neuropathies (Guillain Barré, inflammatory polyneuropathies), Crohn's disease, ulcerative colitis, vasculitis (Wegener's granulomatosus, polyarteritis nodosa), and rare disorders such as polymyalgia rheumatica, temporal arteritis, Sjogren's syndrome, Bechet's disease, Churg-Strauss syndrome, and Takayasu's arteritis; cardiovascular inflammation; gastrointestinal inflammation; infection and immunity; leukocyte biology and immunology; neuroinflammatory disorders; and transplantation, in a warm-blooded animal such as man, said method comprising administering to said animal an effective amount of compound of Formula (I), or a pharmaceutically acceptable salt thereof.

In still a further aspect, there is provided the a method of treating persistent pain states, including neuropathic pain, and pain associated with inflammation, said method comprising administering to said animal an effective amount of compound of Formula (I), or a pharmaceutically acceptable salt thereof.

In yet a further aspect, there is provided a method for producing an anti-proliferative effect in a warm-blooded animal such as man, said method comprising administering to said animal an effective amount of a compound of Formula (I), or a pharmaceutically acceptable salt thereof.

In one aspect, there is provided a method for producing a JAK inhibitory effect in a warm-blooded animal such as man, said method comprising administering to said animal an effective amount of a compound of Formula (I), or a pharmaceutically acceptable salt thereof.

In another aspect, there is provided a method for producing a TRK inhibitory effect in a warm-blooded animal such as man, said method comprising administering to said animal an effective amount of a compound of Formula (I), or a pharmaceutically acceptable salt thereof.

In still another aspect, there is provided a method for treating cancer in a warm-blooded animal such as man, said method comprising administering to said animal an effective amount of a compound of Formula (I), or a pharmaceutically acceptable salt thereof.

In yet another aspect, there is provided a compound of Formula (I), or a pharmaceutically acceptable salt thereof, for use in treating myeloproliferative disorders, myelodysplastic syndrome, and cancer, in a warm-blooded animal such as man.

In a further aspect, there is provided a compound of Formula (I), or a pharmaceutically acceptable salt thereof, for use in treating myeloproliferative disorders, myelodysplastic syndrome, and cancers (solid and hematologic tumors), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acromegaly, acute and chronic inflammation, bone diseases, and ocular diseases with retinal vessel proliferation, in a warm-blooded animal such as man.

In still a further aspect, there is provided a compound of Formula (I), or a pharmaceutically acceptable salt thereof, for use in the treating chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and cancers selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma and leukaemia, in a warm-blooded animal such as man.

In yet a further aspect, there is provided a compound of Formula (I), or a pharmaceutically acceptable salt thereof, for use in the production of an anti-proliferative effect, in a warm-blooded animal such as man.

In one aspect, there is provided a compound of Formula (I), or a pharmaceutically acceptable salt thereof, for use in the production of a JAK inhibitory effect in a warm-blooded animal such as man.

In another aspect, there is provided a compound of Formula (I), or a pharmaceutically acceptable salt thereof, for use in the production of a TRK inhibitory effect in a warm-blooded animal such as man.

In still another aspect, there is provided a compound of Formula (I), or a pharmaceutically acceptable salt thereof, for use in the treatment of cancer in a warm-blooded animal such as man.

In yet another aspect, where reference is made to the Trk inhibitory effect, this may particularly refer to a Trk A inhibitory effect.

In a further aspect, where reference is made to the Trk inhibitory effect, this may particularly refer to a Trk B inhibitory effect.

In still a further aspect, where reference is made to the treatment (or prophylaxis) of cancer, it may particularly refer to the treatment (or prophylaxis) of mesoblastic nephroma, mesothelioma, acute myeloblastic leukemia, acute lymphocytic leukemia, multiple myeloma, oesophageal cancer, myeloma, hepatocellular, pancreatic, cervical cancer, Ewings sarcoma, neuroblastoma, Kaposi's sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma, leukaemia, tumors of the central and peripheral nervous system, melanoma, fibrosarcoma including congenital fibrosarcoma and osteosarcoma. More particularly it refers to prostate cancer. In addition, more particularly it refers to SCLC, NSCLC, colorectal cancer, ovarian cancer and/or breast cancer. In a further aspect it may refer to hormone refractory prostate cancer.

In yet a further aspect, there is provided a pharmaceutical composition comprising a compound of Formula (I), or a pharmaceutically acceptable salt thereof, and at least one pharmaceutically acceptable carrier, diluent, or excipient.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example, polyoxyethylene stearate), or condensation products of ethylene oxide with long chain aliphatic alcohols (for example, heptadecaethyleneoxycetanol), or condensation products of ethylene oxide with partial esters derived from fatty acids and a hexitol such as polyoxyethylene sorbitol monooleate, or condensation products of ethylene oxide with long chain aliphatic alcohols (for example, heptadecaethyleneoxycetanol), or condensation products of ethylene oxide with partial esters derived from fatty acids and a hexitol such as polyoxyethylene sorbitol monooleate, or condensation products of ethylene oxide with partial esters derived from fatty acids and hexitol anhydrides (for example, polyethylene sorbitan monooleate). The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as, for example liquid paraffin, or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example, sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent (for example, a solution in 1,3-butanediol).

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. Accordingly, the optimum dosage may be determined by the practitioner who is treating any particular patient.

The anti-cancer treatment defined herein may be applied as a sole therapy or may involve, in addition to the compound of the invention, conventional surgery or radiotherapy or chemotherapy. Such chemotherapy may include one or more of the following categories of anti-tumor agents:

(i) antiproliferative/antineoplastic drugs and combinations thereof, as used in medical oncology, such as alkylating agents (for example, cis-platin, carboplatin, cyclophosphamide, nitrogen mustard, melphalan, chlorambucil, busulphan and nitrosoureas); antimetabolites (for example, antifolates such as fluoropyrimidines like 5-fluorouracil and tegafur, raltitrexed, methotrexate, cytosine arabinoside and hydroxyurea); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, vinca alkaloids like vincristine, vinblastine, vindesine and vinorelbine and taxoids like taxol and taxotere); and topoisomerase inhibitors (for example, epipodophyllotoxins like etoposide and teniposide, amsacrine, topotecan and camptothecin); and proteosome inhibitors (for example, bortezomib [Velcade®]); and the agent anegrilide [Agrylin®]; and the agent alpha-interferon;

(ii) cytostatic agents such as antioestrogens (for example, tamoxifen, toremifene, raloxifene, droloxifene and iodoxyfene), oestrogen receptor down regulators (for example, fulvestrant), antiandrogens (for example, bicalutamide, flutamide, nilutamide and cyproterone acetate), LHRH antagonists or LHRH agonists (for example, goserelin, leuprorelin and buserelin), progestogens (for example, megestrol acetate), aromatase inhibitors (for example, as anastrozole, letrozole, vorazole and exemestane) and inhibitors of 5α-reductase such as finasteride;

(iii) agents which inhibit cancer cell invasion (for example, metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase (MEK1/2) and for example inhibitors of protein kinase B (PKB/Akt), for example inhibitors of Src tyrosine kinase family and/or Abelson (Abl) tyrosine kinase family such as AZD0530 and dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies and approaches using the immunomodulatory drugs thalidomide and lenalidomide [Revlimid®]; and (x) other treatment regimes including: dexamethasone, proteasome inhibitors (including bortezomib), isotretinoin (13-cis retinoic acid), thalidomide, revemid, Rituxamab, ALIMTA, Cephalon's kinase inhibitors CEP-701 and CEP-2563, anti-Trk or anti-NGF monoclonal antibodies, targeted radiation therapy with 131I-metaiodobenzylguanidine (131I-MIBG), anti-G(D2) monoclonal antibody therapy with or without granulocyte-macrophage colony-stimulating factor (GM-CSF) following chemotherapy.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically-active agent within its approved dosage range.

In addition to its use in therapeutic medicine, compounds of Formula (I) and pharmaceutically acceptable salts are also useful as pharmacological tools in the development and standardization of in vitro and in vivo test systems for the evaluation of the effects of inhibitors of JAK2 in laboratory animals such as cats, dogs, rabbits, monkeys, rats and mice, as part of the search for new therapeutic agents.

In any of the above-mentioned pharmaceutical composition, process, method, use, medicament, and manufacturing features of the instant invention, any of the alternate embodiments of the compounds of the invention described herein also apply.

In one aspect, the inhibition of JAK activity particularly refers to the inhibition of JAK2 activity.

Process

If not commercially available, the necessary starting materials for the procedures such as those described herein may be made by procedures which are selected from standard organic chemical techniques, techniques which are analogous to the synthesis of known, structurally similar compounds, or techniques which are analogous to the Examples, Procedures, and Schemes, described herein.

It is noted that many of the starting materials for synthetic methods as described herein are commercially available and/or widely reported in the scientific literature, or could be made from commercially available compounds using adaptations of processes reported in the scientific literature. The reader is further referred to *Advanced Organic Chemistry*, 5$^{th}$ Edition, by Jerry March and Michael Smith, published by John Wiley & Sons 2001, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, *Protective Groups in Organic Synthesis*, published by John Wiley and Sons, 1991).

Compounds of Formula (I) may be prepared in a variety of ways. The Schemes and Processes shown below illustrate some methods for synthesizing compounds of Formula (I) and intermediates which may be used for the synthesis of compounds of Formula (I) (wherein Q, D, $R^1$, $R^2$, $R^4$, and $R^5$, unless otherwise defined, are as defined hereinabove). Where a particular solvent or reagent is shown in a Scheme or Process, or referred to in the accompanying text, it is to be understood that the chemist of ordinary skill in the art will be able to modify that solvent or reagent as necessary. The Schemes and Processes are not intended to present an exhaustive list of methods for preparing the compounds of Formula (I); rather, additional techniques of which the skilled chemist is aware may be also be used for the compounds' synthesis. The claims are not intended to be limited to the structures shown in the Processes and Schemes.

The skilled chemist will be able to use and adapt the information contained and referenced within the above references, and accompanying examples therein and also the Examples, Procedures, and Schemes herein, to obtain necessary starting materials and products.

In one aspect, compounds of Formula (I) may be prepared by:

1) Process A—reacting a compound of Formula (A):

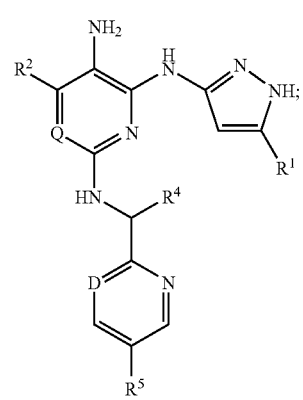

Formula (A)

with a compound of Formula (B):

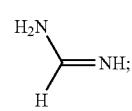

Formula (B)

2) Process B—reacting a compound of Formula (C):

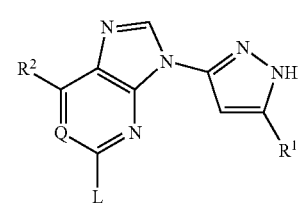

Formula (C)

with a compound of Formula (D):

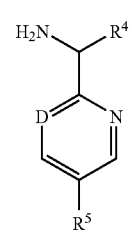

Formula (D)

and thereafter if appropriate:
   i) converting a compound of Formula (I) into another compound of Formula (I);

ii) removing any protecting groups; and/or
iii) forming a pharmaceutically acceptable salt,
wherein
L in each occurrence may be the same or different, and is a leaving group, as discussed hereinabove; and
PG in each occurrence may be the same or different, and is a protecting group, as discussed hereinabove.

Process A—Examples of compounds of Formula (B) include formamidine acetate. Other compounds which advantageously may be used in place of the compounds of Formula (B) include orthoesters such as triethyl orthoformate and triethyl orthoacetate.

Process B—Compounds of Formula (C) and Formula (D) may be reacted together under standard nucleophilic addition reaction conditions. For example, such a reaction may be performed in the presence of a suitable base such as potassium carbonate and a suitable solvent such as DMF and at a temperature range from about 25° C. to about 100° C.

In another aspect, compounds of Formula (A) and compounds of Formula (B) may be reacted together under standard Buchwald conditions (for example see *J. Am. Chem. Soc.*, 118, 7215; *J. Am. Chem. Soc.*, 119, 8451; *J. Org. Chem.*, 62, 1568 and 6066), with a suitable base. Examples of suitable bases include inorganic bases such as cesium carbonate, and organic bases such as potassium t-butoxide. Such a reaction may be advantageously occur in the presence of palladium acetate. Solvents suitable for such a reaction include aromatic solvents such as toluene, benzene, or xylene.

Compounds of Formula (C) may be prepared according to Scheme 1:

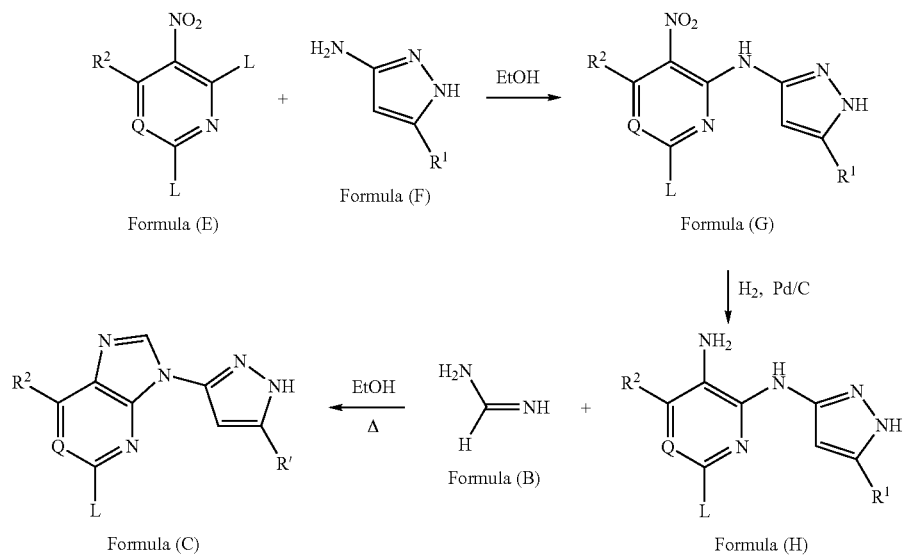

Compounds of Formula (A) may be prepared according to Scheme 2:

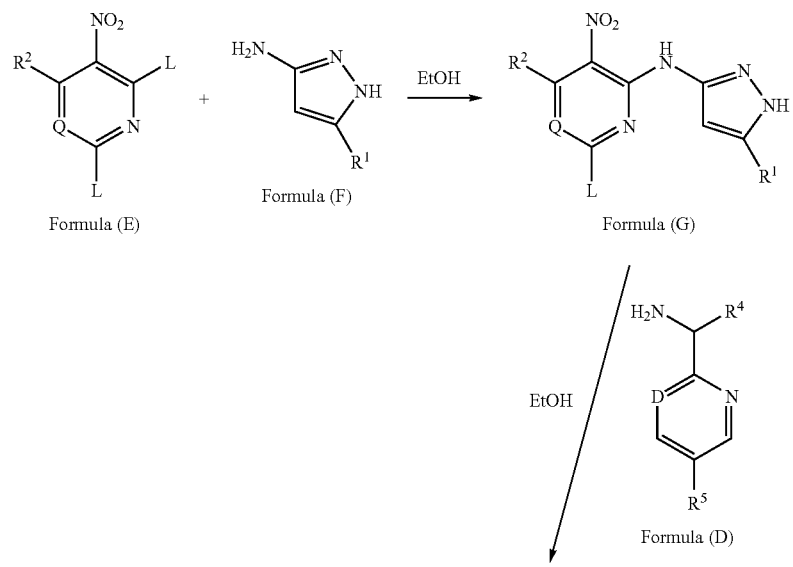

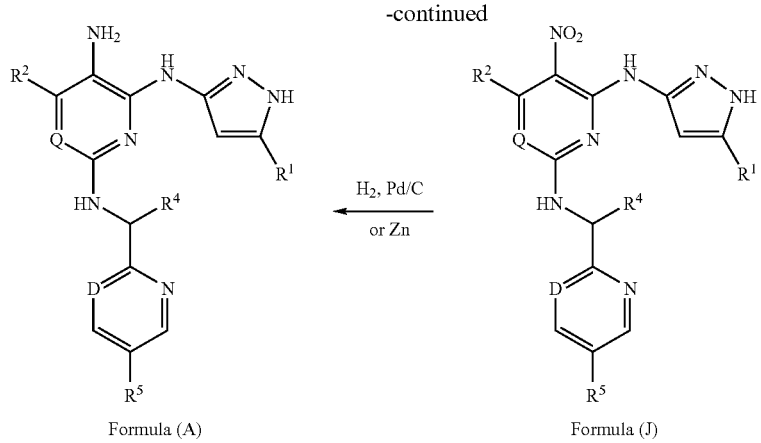

Formula (A)          Formula (J)

The invention will now be further described with reference to the following illustrative examples in which, unless stated otherwise:

(i) temperatures are given in degrees Celsius (° C.); operations are carried out at room temperature or ambient temperature, that is, in a range of 18-25° C.;

(ii) organic solutions were dried over anhydrous magnesium sulfate unless other wise stated; evaporation of organic solvent was carried out using a rotary evaporator under reduced pressure (4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC or liquid chromatography/mass spectroscopy (LCMS) and reaction times are given for illustration only;

(v) final products have satisfactory proton nuclear magnetic resonance (NMR) spectra and/or mass spectra data;

(vi) yields are given for illustration only and are not necessarily those which can be obtained by diligent process development; preparations were repeated if more material was required;

(vii) when given, NMR data is in the form of delta values for major diagnostic protons, given in part per million (ppm) relative to tetramethylsilane (TMS) as an internal standard, determined at 300 MHz in unless otherwise stated;

(viii) chemical symbols have their usual meanings;

(ix) solvent ratio was given in volume:volume (v/v) terms.

(x) "ISCO" refers to normal phase flash column chromatography using pre-packed silica gel cartridges (12 g, 40 g etc.) used according to the manufacturers instruction obtained from ISCO, Inc, 4700 Superior Street Lincoln, Nebr., USA.

(xi) "Biotage" refers to normal phase flash column chromatography using pre-packed silica gel cartridges (12 g, 40 g, 80 g etc.) used according to the manufacturers instruction obtained from Biotage Inc, 1725 Discovery Drive Charlotteville, Va. 22911, USA.

(xii) "Gilson" refers to a YMC-AQC18 reverse phase HPLC Column with dimension 20 mm/100 and 50 mm/250 in H$_2$O/MeCN with 0.1% TFA as mobile phase unless otherwise stated and used according to the manufacturers instruction obtained from Gilson, Inc. 3000 Parmenter Street, Middleton, Wis. 53562-0027, U.S.A.

(xiii) Parr Hydrogenator or Parr shaker type hydrogenators are systems for treating chemicals with hydrogen in the presence of a catalyst at pressures up to 5 atmospheres (60 psi) and temperatures to 80° C.

(xiv) the following abbreviations have been used:

| | |
|---|---|
| DCM | dichloromethane; |
| HPLC | high-performance liquid chromatography; and |
| DIPEA | N,N-diisopropylethylamine |
| DMF | N,N-dimethylformamide; |
| THF | tetrahydrofuran; |
| DMAP | 4-dimethylaminopyridine; |
| DMSO | dimethylsulphoxide; |
| EtOAc | ethyl acetate; |
| Et$_2$O | diethyl ether; |
| Boc$_2$O | t-butyloxycarbonyl anhydride; |
| GC | Gas Chromatography; |
| MTBE | methyl t-butyl ether; |
| DMAC | N,N-dimethyl acetamide; |
| Pd$_2$(dba)$_3$ | Tris(dibenzylideneacetone)dipalladium(0); |
| NMP | N-methylpyrrolidone; |
| dppf | 1,1'-bis(diphenylphosphino)ferrocene; |
| t-BuLi | t-butyllithium; |
| MeOH | methanol; |
| EtOH | ethanol; |
| n-BuOH | n-butanol; |
| Oxone ® | potassium peroxomonosulfate; |
| HATU | O-(7-Azabenzotriazole-1-yl)-N,N,N'N'-tetramethyluronium hexafluorophosphate |

Intermediate 1

5-Fluoropyridine-2-carbonitrile

2-Bromo-5-fluoropyridine (93.0 g, 528 mmol), Zn dust (8.29 g, 127 mmol), zinc cyanide (40.3 g, 343 mmol), 1,1'-bis(diphenylphosphino)ferrocene (11.7 g, 21.1 mmol) and Pd$_2$dba$_3$ (9.68 g, 10.6 mmol) in anhydrous DMAc (300 ml) was heated at 95° C. for 3 hours. After cooled to room temperature, brine (100 ml) and ether (500 ml) was added. The solid formed was removed by filtration and washed with ether (300 ml). The organic layer was separated, washed with brine (200 ml) and dried over sodium sulfate, and concentrated. After removal of solvent, the resulted residue was purified by column chromatography (hexane-DCM=1:1) to give the title compound as a white solid (49 g, 72%). $^1$H NMR (400 MHz, DMSO-d6) δ 8.82 (d, J=2.8 Hz, 1H), 8.21 (dd, J=4.4 and 8.8 Hz, 1H), 8.05 (dd, J=2.8 and 8.8 Hz, 1H).

Intermediate 2

N-(1-(5-Fluoropyridin-2-yl)vinyl)acetamide

A solution of MeMgBr (170.3 ml, 510.98 mmol) in ether was diluted with 170 ml of anhydrous THF and cooled to 0° C. 5-fluoropyridine-2-carbonitrile (Intermediate 1, 53.6 g, 425.82 mmol) in THF (170 ml) was added dropwise. The reaction was stirred at 0° C. for 30 minutes, then diluted with dichloromethane (170 ml). Acetic anhydride (48.3 ml, 510.98 mmol) in dichloromethane (100 ml) was added dropwise at 0° C. After addition, the reaction was warmed to room temperature and stirred at room temperature for 8 hours. Saturated sodium bicarbonate solution (50 ml) was added and extracted with EtOAc (2×200 ml). The combined organic was dried over sodium sulfate. After removal of solvent, the resulted residue was purified by column chromatography (hexane: EtOAc=2.5:1) to give the title compound as a white solid (26.6 g, 35%). $^1$H NMR (400 MHz) δ 9.37 (s, 1H), 8.57 (d, J=2.8 Hz, 1H), 7.81 (m, 2H), 6.01 (s, 1H), 5.52 (s, 1H), 2.08 (s, 3H). MS: Calculated: 180. Found: [M+H]$^+$ 181.

Intermediate 3

(S)—N-(1-(5-Fluoropyridin-2-yl)ethyl)acetamide

To a solution of N-(1-(5-fluoropyridin-2-yl)vinyl)acetamide (Intermediate 2, 11.0 g, 61.1 mmol) in MeOH (120 ml) under $N_2$ was added (+)-1,2-bis((2S,5S)-2,5-diethylphospholano)benzene(cyclooctadiene)rhodium(I)trifluoromethanesulfonate (0.441 g, 0.611 mmol). The solution was transferred to a high pressure bomb and charged 150 psi $H_2$. The reaction stirred at room temperature and maintained inside pressure between 120-150 psi for 7 hours. The solvent was removed and the resulted residue was purified by column chromatography (EtOAc) to give the title compound as a white solid (9.8 g, 88%). $^1$H NMR (400 MHz) δ 8.49 (d, J=2.4 Hz, 1H), 8.32 (d, J=7.6 Hz, 1H), 7.66 (m, 1H), 7.39 (dd, J=4.4 and 8.8 Hz, 1H), 4.95 (m, 1H), 1.85 (s, 3H), 1.34 (d, J=7.2 Hz, 3H). MS: Calculated: 182. Found: [M+H]$^+$ 183. Enantiomeric excess determined by HPLC (Chiralpak IA; 70:30 $CO_2$/MeOH), 95.3% ee.

Intermediate 4 tert-Butyl[(1S)-1-(5-fluoropyridin-2-yl)ethyl]carbamate

A solution of (S)—N-(1-(5-fluoropyridin-2-yl)ethyl)acetamide (Intermediate 3, 11.0 g, 60.37 mmol), DMAP (1.48 g, 12.07 mmol) and Boc$_2$O (26.35 g, 120.7 mmol) in THF (100 ml) was stirred at 50° C. for 20 hours. After cooled to room temperature, lithium hydroxide monohydrate (5.19 g, 123.8 mmol) and water (100 ml) were added. The reaction was stirred at room temperature for 5 hours and diluted with ether (200 ml). The organic layer was separated, washed with brine (100 ml), and dried over sodium sulfate. After removal of solvent, the resulted residue was purified by column chromatography (Hexane-EtOAc=5:1) to give the title compound as a pale yellow oil (13.6 g, 94%). $^1$H NMR (400 MHz) δ 8.46 (d, J=2.8 Hz, 1H), 7.69 (m, 1H), 7.35-7.41 (m, 2H), 4.67 (m, 1H), 1.37 (s, 9H), 1.32 (d, J=7.2 Hz, 3H). MS: Calculated: 240. Found: [M+H]$^+$ 241.

Intermediate 5

[(1S)-1-(5-Fluoropyridin-2-yl)ethyl]amine hydrochloride

To a solution of tert-Butyl[(1S)-1-(5-fluoropyridin-2-yl)ethyl]carbamate (Intermediate 4, 12.8 g, 53.3 mmol) in dichloromethane (100 ml) was added HCl/dioxane solution (107 ml, 4 N, 428 mmol). The reaction was stirred at room temperature for 3 hours. The solvent was removed and 50 ml of saturated sodium bicarbonate was added. The resulting aqueous solution was extracted with ether (6×400 ml), dried over sodium sulfate and concentrated to give the title compound (7.30 g, 98%) as pale yellow oil. $^1$H NMR (400 MHz) δ 8.44 (d, J=2.8 Hz, 1H), 7.66 (m, 1H), 7.53 (m, 1H), 4.01 (q, J=6.8 Hz, 1H), 1.94 (b, 2H), 1.26 (d, J=6.8 Hz, 3H). MS: Calcd.: 140. Found: [M+H]$^+$ 141.

Intermediate 6

5-Isopropoxy-1H-pyrazol-3-amine

The title compound may be prepared via the following procedure: To a suspension of 3-amino-5-hydroxypyrazole (0.50 mol) in $CH_2Cl_2$ is added triphenylphosphine (0.59 mol) and the resulting mixture is cooled to 0° C. Diisopropyl azodicarboxylate (0.59 mol) is added drop-wise over a period of 35 minutes (the temperature of the reaction mixture is kept below 2° C.) to give a suspension. The reaction mixture is then held at 0° C. for 1 hour. A precipitate may be observed after 30 minutes of the reaction. Isopropyl alcohol (1.25 mol) is then added drop-wise over a period of 30 minutes at 0° C. as the slurry thins considerably to give a suspension. The reaction mixture is then held at 0° C. for 1 hour. The reaction mixture is warmed slowly to ambient temperature and is then held at ambient temperature overnight. The reaction mixture is filtered to remove undissolved solids. The filtrate is dried (MgSO$_4$) and concentrated under reduced pressure to give an oil. Purification by column chromatography (5%→10% MeOH in $CH_2Cl_2$) affords the title compound. (400 MHz, DMSO-d6) δ ppm 10.3 (br s, 1H), 4.84 (br s, 2H), 4.65 (s, 1H), 4.52 (m, 1H), 1.20 (m, 6H).

Intermediate 7

6-Chloro-N-(5-isopropoxy-1H-pyrazol-3-yl)-3-nitropyridin-2-amine

A mixture of 2,6-dichloro-3-nitropyridine (0.5 g) and 5-isopropoxy-1H-pyrazol-3-amine (Intermediate 6, 0.35 g) in acetonitrile (10 mL) with triethylamine (2 mL) was stirred at room temperature for 24 hours, The resulting mixture was concentrated, and the resulting residue was separated by silica gel column (Hexane/Ethyl acetate) to afford 0.45 g desired product. MS (electrospray): 298 (M+1) for $C_{11}H_{12}ClN_5O_3$.

Intermediate 8

$N^6$-[(1S)-1-(5-Fluoropyridin-2-yl)ethyl]-$N^2$-(5-isopropoxy-1H-pyrazol-3-yl)-3-nitropyridine-2,6-diamine A mixture of 6-chloro-N-(5-isopropoxy-1H-pyrazol-3-yl)-3-nitropyridin-2-amine (Intermediate 7, 0.8 g) and [(1S)-1-(5-fluoropyridin-2-yl)ethyl]amine hydrochloride (Intermediate 5, 0.4 g) in n-BuOH (10 mL) with diisopropylethylamine (2 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.6 g of desired product. MS (electrospray): 402 (M+1) for $C_{18}H_{20}FN_7O_3$. $^1$H NMR (300 MHz, DMSO-d6) δ ppm 12.3 (s, 1H) 11.0 (s, 1H) 8.80 (m, 1H) 8.50 (m, 1H) 8.15 (m, 1H) 7.80 (m, 1H) 7.30 (m, 1H) 6.20 (d, 1H) 5.80 (m, 1H) 5.35 (m, 1H), 4.60 (m, 1H) 1.50 (d, 3H) 1.20 (d, 6H).

Intermediate 9

6-Chloro-N-(5-cyclopropyl-1H-pyrazol-3-yl)-3-nitropyridin-2-amine

A mixture of 2,6-dichloro-3-nitropyridine (5 g) and 5-cyclopropyl-1H-pyrazol-3-amine (5 g) in acetonitrile (40 mL) with diisopropylethylamine (6 mL) was stirred at room temperature for 24 hours, The resulting mixture was concentrated, and the resulting residue was separated by silica gel column (Hexane/Ethyl acetate) to afford 5 g desired product. MS (electrospray): 280 (M+1) for $C_{11}H_{10}ClN_5O_2$. $^1$H NMR (300 MHz, $CD_3OD$) δ ppm 8.5 (d, 1H) 6.9 (d, 1H) 6.5 (s, 1H) 1.9 (m, 1H) 1.0 (m, 2H) 0.70 (m, 2H).

Intermediate 10

$N^2$-(5-Cyclopropyl-1H-pyrazol-3-yl)-$N^6$-[(1S)-1-(5-fluoropyridin-2-yl)ethyl]-3-nitropyridine-2,6-diamine A mixture of 6-chloro-N-(5-cyclopropyl-1H-pyrazol-3-yl)-3-nitropyridin-2-amine (Intermediate 9, 0.5 g) and [(1S)-1-(5-fluoropyridin-2-yl)ethyl]amine hydrochloride (Intermediate 5, 0.35 g) in n-BuOH (10 mL) with diisopropylethylamine (1 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.45 g of desired product. MS (electrospray): 384 (M+1) for $C_{18}H_{18}FN_7O_2$. $^1$H NMR (300 MHz, $CD_3OD$) δ ppm 8.60 (s, 1H) 8.20 (m, 1H) 8.15 (m, 1H) 7.60 (m, 1H) 7.40 (s, 1H) 6.30 (d, 1H) 6.20 (s, 1H) 5.35 (m, 1H), 1.90 (m, 1H) 1.60 (d, 3H) 1.00 (m, 2H) 0.80 (m, 2H).

Intermediate 11

5-Fluoropyrimidine-2-carbonitrile

A 10 ml microwave vial was charged with 2-chloro-5-fluoropyrimidine (2.0 g, 15.09 mmol), $Pd_2(dba)_3$ (0.549 g, 0.6 mmol), dppf (0.67 g, 1.21 mmol), zinc cyanide (1.15 g, 9.81 mmol), and zinc dust (0.237 mg, 3.62 mmol). The flask was evacuated and backfilled with $N_2$, and anhydrous DMAc. The vial was mounted onto a Personal Chemistry microwave reactor and heated at 100° C. for 10 hours. The reaction mixture was diluted with EtOAc and then washed with brine three times. The organic layer was obtained and evaporated to dryness. The dried residue was purified by silica gel chromatography (By ISCO Combiflash with gradient EtOAc and hexanes) to afford the title compound as a creamy solid (1.50 g, 80%). GC-MS: 123 (M); $^1$H NMR ($CDCl_3$) δ 8.80 (s, 2H).

Intermediate 12

N-(1-(5-Fluoropyrimidin-2-yl)vinyl)acetamide

5-Fluoropyrimidine-2-carbonitrile (Intermediate 11, 1.0 g, 8.1 mmol) in THF (10 ml) was added a solution of MeMgBr (3.3 ml, 9.75 mmol) in ether drop wise at 0° C. After addition, the reaction was warmed to room temperature, stirred at room temperature for 1 hour and then diluted with DCM (10 ml). Acetic anhydride (1.23 ml, 13.0 mmol) was added in one portion. The reaction was stirred at room temperature for 1 hour and 40° C. for 1 hour. Saturated sodium bicarbonate solution (10 ml) was added and extracted with EtOAc (2×20 ml). The combined organic was dried over sodium sulfate. After removal of solvent, the resulted residue was purified by column chromatography (hexane:EtOAc=2.5:1) to give the title compound as a white solid (0.38 g, 26%). $^1$H NMR (400 MHz) 9.34 (s, 1H), 8.95 (s, 2H), 6.25 (s, 1H), 6.03 (s, 1H), 2.11 (s, 3H). MS: Calculated: 181. Found: $[M+H]^+$ 182.

Intermediate 13

(S)—N-(1-(5-Fluoropyrimidin-2-yl)ethyl)acetamide

N-(1-(5-Fluoropyrimidin-2-yl)vinyl)acetamide (Intermediate 12, 0.10 g, 0.55 mmol) in MeOH (5 ml) under $N_2$ was added (+)-1,2-bis((2S,5S)-2,5-diethylphospholano)benzene (cyclooctadiene)rhodium(I)trifluoromethanesulfonate (0.04 g, 0.0055 mmol). The solution was transferred to a high-pressure bomb and charged 150 psi $H_2$. The reaction was stirred at room temperature for 4 hours. The solvent was removed and the resulted residue was purified by column chromatography (EtOAc) to give the title compound as a white solid (0.096 g, 95%). $^1$H NMR (400 MHz) 8.84 (d, J=0.8 Hz, 2H), 8.34 (d, J=7.6 Hz, 1H), 5.00 (m, 1H), 1.84 (s, 3H), 1.37 (d, J=6.8 Hz, 3H). MS: Calculated: 183. Found: $[M+H]^+$ 184. Enantiomeric excess determined by HPLC (Chiralpak IA; 95:5 $CO_2$/MeOH), >99% ee.

Intermediate 14 tert-Butyl[(1S)-1-(5-fluoropyrimidin-2-yl)ethyl]carbamate (S)—N-(1-(5-Fluoropyrimidin-2-yl)ethyl)acetamide (Intermediate 13, 0.20 g, 1.09 mmol), DMAP (0.027 g, 0.22 mmol) and di-tert-butyl-dicarbonate (0.60 g, 2.73 mmol) in THF (10 ml) was stirred at 50° C. for 40 hours. After cooling to room temperature, lithium hydroxide monohydrate (0.094 g, 2.24 mmol) and water (10 ml) was added. The reaction was stirred at room temperature for 9 hours. Ether (30 ml) was added, organic layer was separated, washed with brine (20 ml) and dried over sodium sulfate. After removal of solvent, the resulted residue was purified by column chromatography (Hex-EtOAc=5:1) to give the title compound as a pale yellow oil (0.21 g, 80%). NMR (400 MHz) 8.84 (s, 2H), 7.24 (d, J=7.6 Hz, 1H), 4.74 (m, 1H), 1.35 (s, 12H). MS: Calculated: 241. Found: $[M+H]^+$ 242.

Intermediate 15

[(1S)-1-(5-Fluoropyrimidin-2-yl)ethyl]amine hydrochloride

To a solution of tert-butyl[(1S)-1-(5-fluoropyrimidin-2-yl) ethyl]carbamate (Intermediate 14, 0.21 g, 0.87 mmol) in DCM (5 ml) was added HCl (1.3 ml, 5.2 mmol) in dioxane.

Intermediate 16

N²-(5-Cyclopropyl-1H-pyrazol-3-yl)-N⁶-[(1S)-1-(5-fluoropyrimidin-2-yl)ethyl]-3-nitropyridine-2,6-diamine A mixture of 6-chloro-N-(5-cyclopropyl-1H-pyrazol-3-yl)-3-nitropyridin-2-amine (Intermediate 9, 0.5 g) and [(1S)-1-(5-fluoropyrimidin-2-yl)ethyl]amine hydrochloride (Intermediate 15, 0.35 g) in n-BuOH (10 mL) with diisopropylethylamine (1 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.5 g of desired product. MS (electrospray): 385 (M+1) for $C_{17}H_{18}FN_8O_2$. ¹H NMR (300 MHz, CD₃OD) δ ppm 8.70 (s, 2H) 8.20 (d, 1H) 6.40 (m, 1H) 6.20 (d, 1H) 5.45 (m, 1H), 1.90 (m, 1H) 1.70 (d, 3H) 1.05 (m, 2H) 0.90 (m, 2H).

Intermediate 17

2-Chloro-N-(5-cyclopropyl-1H-pyrazol-3-yl)-5-nitropyrimidin-4-amine

A mixture of 2,4-dichloro-5-nitropyrimidine (2 g) and 5-cyclopropyl-1H-pyrazol-3-amine (2 g) in acetonitrile (20 mL) with diisopropylethylamine (2 mL) was stirred at room temperature for 24 hours, The resulting mixture was concentrated, and the resulting residue was separated by silica gel column (Hexane/Ethyl acetate) to afford 2.1 g desired product. MS (electrospray): 281 (M+1) for $C_{10}H_9ClN_6O_2$.

Intermediate 18

N⁴-(5-Cyclopropyl-1H-pyrazol-3-yl)-N²-[(1S)-1-(5-fluoropyrimidin-2-yl)ethyl]-5-nitropyrimidine-2,4-diamine A mixture of 2-chloro-N-(5-cyclopropyl-1H-pyrazol-3-yl)-5-nitropyrimidin-4-amine (Intermediate 17, 0.35 g) and [(1S)-1-(5-fluoropyrimidin-2-yl)ethyl]amine hydrochloride (Intermediate 15, 0.25 g) in n-BuOH (10 mL) with diisopropylethylamine (1 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.3 g of desired product. MS (electrospray): 386 (M+1) for $C_{16}H_{16}FN_9O_2$. ¹H NMR (300 MHz, DMSO-d6) δ ppm 12.4 (s, 1H) 11.30 (s, 1H) 9.15 (s, 1H) 9.00 (s, 1H) 8.80 (s, 2H) 6.10 (d, 1H) 5.25 (m, 1H), 1.90 (m, 1H) 1.60 (d, 3H) 1.00 (m, 2H) 0.80 (m, 2H).

Intermediate 19

N⁴-(5-Cyclopropyl-1H-pyrazol-3-yl)-N²-[(1S)-1-(5-fluoropyridin-2-yl)ethyl]-5-nitropyrimidine-2,4-diamine A mixture of 2-chloro-N-(5-cyclopropyl-1H-pyrazol-3-yl)-5-nitropyrimidin-4-amine (Intermediate 17, 0.35 g) and [(1S)-1-(5-fluoropyridin-2-yl)ethyl]amine hydrochloride (Intermediate 5, 0.25 g) in n-BuOH (10 mL) with diisopropylethylamine (1 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.3 g of desired product. MS (electrospray): 385 (M+1) for $C_{17}H_{16}FN_8O_2$.

Intermediate 20

N⁶-[(1S)-1-(5-Fluoropyrimidin-2-yl)ethyl]-N²-(5-isopropoxy-1H-pyrazol-3-yl)-3-nitropyridine-2,6-diamine A mixture of 6-chloro-N-(5-isopropoxy-1H-pyrazol-3-yl)-3-nitropyridin-2-amine (Intermediate 7, 0.4 g) and [(1S)-1-(5-fluoropyrimidin-2-yl)ethyl]amine hydrochloride (Intermediate 15, 0.25 g) in n-BuOH (5 mL) with diisopropylethylamine (1.5 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.55 g of desired product. MS (electrospray): 403 (M+1) for $C_{17}H_{19}FN_8O_3$. ¹H NMR (300 MHz, CD₃OD) δ ppm 8.40 (s, 2H) 8.10 (d, 1H) 6.15 (d, 1H) 5.60 (s, 1H) 5.35 (m, 1H), 4.60 (m, 1H) 1.50 (d, 3H) 1.20 (d, 6H).

Intermediate 21

(R)—N-(2-{[tert-Butyl(dimethyl)silyl]oxy}ethylidene)-2-methylpropane-2-sulfinamide To a solution of (R)-2-methylpropane-2-sulfinamide (2.5 g, 20.6 mmol) and {[tert-butyl(dimethyl)silyl]oxy}acetaldehyde (4.32 ml, 22.7 mmol) in CH₂Cl₂ (30 ml) was added CuSO₄ (7.23 g, 45.32 mmol). The reaction mixture was stirred at room temperature for 2 days. The mixture was filtered through Centel), washed with CH₂Cl₂ and concentrated in vacuo. Column chromatography (0-30% EtOAc in hexanes) gave the desired product (R)—N-(2-{[tert-butyl(dimethyl)silyl]oxy}ethylidene)-2-methylpropane-2-sulfinamide (Tetrahedron Lett. 2001, 42, 2051-54). ¹H NMR (300 MHz, CDCl₃) δ 7.86-8.24 (m, 1H) 4.53 (d, J=3.01 Hz, 2H) 1.15-1.23 (m, 9H) 0.90 (s, 9H) 0.08 (s, 6H).

Intermediate 22

($R_S$)—N-[(1R)-2-{[tert-Butyl(dimethyl)silyl]oxy}-1-(5-fluoropyridin-2-yl)ethyl]-2-methylpropane-2-sulfinamide*

To a cold solution of 2-bromo-5-fluoropyridine (1.3 g, 7.2 mmol) in Et₂O (8 ml) at −68° C. was added a solution of t-BuLi (1.7 M in pentane, 8.5 ml, 14.4 mmol) carefully. The temperature of the mixture was kept below −65° C. and the mixture was allowed to stir for 15 minutes at −70° C. A solution of (R)—N-(2-{[tert-butyl(dimethyl)silyl]oxy}ethylidene)-2-methylpropane-2-sulfinamide (Intermediate 21, 1.0 g, 3.6 mmol) in Et₂O (24 ml) was cooled to −75° C. To it was cannulated a solution of the above lithium compound for a duration of 15 minutes. More Et₂O (2 ml) was used to rinse the lithium compound solution. The mixture was allowed to stir at −78° C. for 3 hours. To it was added saturated NH₄Cl solution. EtOAc was added and the organic layer was washed with brine and concentrated. Column chromatography (20-40% EtOAc in hexanes) gave the desired product ($R_S$)—N-[(1R)-2-{[tert-butyl(dimethyl)silyl]oxy}-1-(5-fluoropyridin-2-yl)ethyl]-2-methylpropane-2-sulfinamide* as a solid (higher Rf on TLC, 1.19 g) together with diastereoisomer (lower Rf on TLC, 166 mg). $^1$H NMR (300 MHz, CDCl$_3$) ☐ ppm 8.41 (s, 1H) 7.35 (d, J=6.78 Hz, 2H) 4.59 (t, J=5.65 Hz, 1H) 4.43 (d, J=5.28 Hz, 1H) 3.82-4.02 (m, 2H) 1.23 (s, 9H) 0.81 (s, 9H)-0.06 (d, J=12.06 Hz, 6H).

* "$R_S$" is intended to denote that the sulfur has an R configuration.

Intermediate 23

(2R)-2-Amino-2-(5-fluoropyridin-2-yl)ethanol hydrochloride

To a solution of ($R_S$)—N-[(1R)-2-{[tert-butyl(dimethyl)silyl]oxy}-1-(5-fluoropyridin-2-yl)ethyl]-2-methylpropane-2-sulfinamide (Intermediate 22, 1.13 g, 3.02 mmol) in MeOH (15 ml) was added hydrochloric acid (4 M in dioxane, 3.02 ml, 12.08 mol) at 0° C. and the mixture was stirred for 15 minutes and was concentrated. The mixture was triturated from hexanes to provide the title salt (575 mg). The product is highly hygroscopic. $^1$H NMR (300 MHz, DMSO-d6) δ ppm 8.62 (s, 1H) 8.55 (s, 2H) 7.76-7.93 (m, 1H) 7.65 (dd, J=8.29, 4.52 Hz, 1H) 4.43 (d, J=4.52 Hz, 1H) 3.77 (s, 2H).

Intermediate 24

(2R)-2-(5-Fluoropyridin-2-yl)-2-({6-[(5-isopropoxy-1H-pyrazol-3-yl)amino]-5-nitropyridin-2-yl}amino) ethanol A mixture of 6-chloro-N-(5-isopropoxy-1H-pyrazol-3-yl)-3-nitropyridin-2-amine (Intermediate 7, 0.5 g) and (2R)-2-amino-2-(5-fluoropyridin-2-yl)ethanol hydrochloride (Intermediate 23, 0.45 g) in n-BuOH (10 mL) with diisopropylethylamine (3 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.45 g of desired product. MS (electrospray): 418 (M+1) for $C_{18}H_{20}FN_7O_4$. $^1$H NMR (300 MHz, CD$_3$OD) δ ppm 8.50 (s, 1H) 8.20 (d, 1H) 7.60 (s, 1H) 7.45 (s, 1H) 6.30 (s, 1H) 5.70 (s, 1H) 5.45 (m, 1H), 4.60 (m, 1H) 3.90 (m, 2H) 1.30 (d, 6H).

Intermediate 25

5-Ethoxy-1H-pyrazol-3-amine

The title compound was prepared using a procedure similar to the one described for the synthesis of Intermediate 6, using 3-amino-5-hydroxypyrazole as the starting material. (400 MHz, CD$_3$OD) ☐ ppm 4.85 (br s, 3H), 4.02 (m, 2H), 1.30 (t, J=8 Hz, 3H)

Intermediate 26

6-Chloro-N-(5-ethoxy-1H-pyrazol-3-yl)-3-nitropyridin-2-amine

The title compound was prepared using a procedure similar to the one described for the synthesis of Intermediate 7, using Intermediate 25 as the starting material. MS (electrospray): 284 (M+1) for $C_{10}H_{10}ClN_5O$.

Intermediate 27

(2R)-2-({6-[(5-Ethoxy-1H-pyrazol-3-yl)amino]-5-nitropyridin-2-yl}amino)-2-(5-fluoropyridin-2-yl) ethanol A mixture of 6-chloro-N-(5-ethoxy-1H-pyrazol-3-yl)-3-nitropyridin-2-amine (Intermediate 26, 0.2 g) and (2R)-2-amino-2-(5-fluoropyridin-2-yl)ethanol hydrochloride (Intermediate 23, 0.15 g) in n-BuOH (5 mL) with diisopropylethylamine (1 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.2 g of the title compound. MS (electrospray): 404 (M+1) for $C_{17}H_{18}FN_7O_4$.

Intermediate 28

$N^2$-(5-Ethoxy-1H-pyrazol-3-yl)-$N^6$-[(1S)-1-(5-fluoropyrimidin-2-yl)ethyl]-3-nitropyridine-2,6-diamine A mixture of 6-chloro-N-(5-ethoxy-1H-pyrazol-3-yl)-3-nitropyridin-2-amine (Intermediate 26, 0.35 g) and [(1S)-1-(5-fluoropyrimidin-2-yl)ethyl]amine hydrochloride (Intermediate 15, 0.20 g) in n-BuOH (5 mL) with diisopropylethylamine (1 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.37 g of the title compound. MS (electrospray): 389 (M+1) for $C_{16}H_{17}FN_8O_3$.

Intermediate 29

$N^2$-(5-Ethoxy-1H-pyrazol-3-yl)-$N^6$-[(1S)-1-(5-fluoropyridin-2-yl)ethyl]-3-nitropyridine-2,6-diamine A mixture of 6-chloro-N-(5-ethoxy-1H-pyrazol-3-yl)-3-nitropyridin-2-amine (Intermediate 26, 0.35 g) and [(1S)-1-(5-fluoropyridin-2-yl)ethyl]amine hydrochloride (Intermediate 5, 0.20 g) in n-BuOH (5 mL) with diisopropylethylamine (1 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.37 g of the title compound. MS (electrospray): 388 (M+1) for $C_{17}H_{17}FN_7O_3$.

Intermediate 30

2-Chloro-N-(5-isopropoxy-1H-pyrazol-3-yl)-5-nitropyrimidin-4-amine

A mixture of 2,4-dichloro-5-nitropyrimidine (2 g) and 5-isopropoxy-1H-pyrazol-3-amine (Intermediate 6, 1.5 g) in acetonitrile (50 mL) with triethylamine (5 mL) was stirred at room temperature for 24 hours, The resulting mixture was concentrated, and the resulting residue was separated by silica gel column (Hexane/Ethyl acetate) to afford 1 g of the title compound. MS (electrospray): 299 (M+1) for $C_{10}H_{12}ClN_6O_3$.

Intermediate 31

N$^2$-[(1S)-1-(5-Fluoropyridin-2-yl)ethyl]-N$^4$-(5-isopropoxy-1H-pyrazol-3-yl)-5-nitropyrimidine-2,4-diamine A mixture of 2-chloro-N-(5-isopropoxy-1H-pyrazol-3-yl)-5-nitropyrimidin-4-amine (Intermediate 30, 1.0 g) and [(1S)-1-(5-fluoropyridin-2-yl)ethyl]amine hydrochloride (Intermediate 5, 0.8 g) in n-BuOH (5 mL) with diisopropylethylamine (1 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 1.0 g of the title compound. MS (electrospray): 403 (M+1) for C$_{17}$H$_{19}$FN$_8$O$_3$. $^1$H NMR (300 MHz, CD$_3$OD) δ ppm 9.10 (s, 1H) 8.50 (s, 1H) 7.60 (m, 1H) 7.40 (m, 1H) 5.80 (s, 1H) 5.20 (m, 1H) 4.70 (m, 2H) 1.60 (d, 3H) 1.40 (d, 6H).

Intermediate 32

N$^2$-[(1S)-1-(5-Fluoropyrimidin-2-yl)ethyl]-N$^4$-(5-isopropoxy-1H-pyrazol-3-yl)-5-nitropyrimidine-2,4-diamine A mixture of 2-chloro-N-(5-isopropoxy-1H-pyrazol-3-yl)-5-nitropyrimidin-4-amine (Intermediate 30, 0.2 g) and [(1S)-1-(5-fluoropyrimidin-2-yl)ethyl]amine hydrochloride (Intermediate 15, 0.15 g) in n-BuOH (5 mL) with diisopropylethylamine (1 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.2 g of title compound. MS (electrospray): 404 (M+1) for C$_{16}$H$_{18}$FN$_9$O$_3$.

Intermediate 33

(S)—N-[(5-Fluoropyridin-2-yl)methylene]-2-methylpropane-2-sulfinamide

The title compound was prepared using a procedure similar to the one described for the synthesis of Intermediate 21, using 5-fluoropyridine-2-carbaldehyde and (S)-2-methylpropane-2-sulfinamide as the starting materials. $^1$H NMR (300 MHz, CDCl$_3$) δ ppm 8.67 (s, 1H) 8.58 (s, 1H) 8.06 (dd, J=8.29, 4.52 Hz, 1H) 7.51 (t, J=7.91 Hz, 1H) 1.20-1.33 (m, 9H). The product was used without purification.

Intermediate 34

(Ss)-N-[(1S)-1-(5-Fluoropyridin-2-yl)propyl]-2-methylpropane-2-sulfinamide*

To a solution of (S)—N-[(5-fluoropyridin-2-yl)methylene]-2-methylpropane-2-sulfinamide (Intermediate 33, 1.5 g, 6.58 mmol) in CH$_2$Cl$_2$ (10 ml) at −45° C. was added ethylmagnesium bromide (1.0 M in MTBE, 6.6 ml, 6.6 mmol) dropwise. The reaction mixture was stirred at −40° C. for 30 minutes and to it was added water. The layers were separated and the organic layer was concentrated. Column chromatography on silica gel (30-50% EtOAc in CH$_2$Cl$_2$) gave the title compound (higher Rf on TLC) as a solid (485 mg, 29%). $^1$H NMR (300 MHz, CDCl$_3$) δ ppm 8.39 (d, J=3.01 Hz, 1H) 7.29-7.41 (m, 1H) 7.21-7.24 (m, 1H) 4.60 (d, J=7.54 Hz, 1H) 4.31 (q, J=6.78 Hz, 2H) 1.22-1.27 (s, 9H) 0.86 (t, J=7.54 Hz, 3H).

* "Ss" is intended to denote that the sulfur has an S configuration.

Intermediate 35

[(1S)-1-(5-Fluoropyridin-2-yl)propyl]amine

The title compound was prepared using a procedure similar to the one described for the synthesis of Intermediate 21, using (Ss)-N-[(1S)-1-(5-fluoropyridin-2-yl)propyl]-2-methylpropane-2-sulfinamide (Intermediate 34) as the starting material. $^1$H NMR (300 MHz, DMSO-d6) δ ppm 8.64 (s, 1H) 8.59 (s, 2H) 7.77-7.92 (m, 1H) 7.64 (dd, J=8.29, 4.52 Hz, 1H) 4.33 (d, J=7.54 Hz, 1H) 1.72-1.97 (m, 2H) 0.75 (t, J=7.54 Hz, 3H).

Intermediate 36

[(1S)-1-(5-Fluoropyridin-2-yl)propyl]-N$^2$-(5-isopropoxy-1H-pyrazol-3-yl)-3-nitropyridine-2,6-diamine A mixture of 6-chloro-N-(5-isopropoxy-1H-pyrazol-3-yl)-3-nitropyridin-2-amine (Intermediate 7, 0.5 g) and [(1S)-1-(5-fluoropyridin-2-yl)propyl]amine (Intermediate 35, 0.45 g) in n-BuOH (10 mL) with diisopropylethylamine (3 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 0.45 g of desired product. MS (electrospray): 416 (M+1) for C$_{19}$H$_{22}$FN$_7$O$_3$.

Intermediate 37

2,4,6-Trichloro-5-nitro-pyrimidine

A solution of 5-nitropyrimidine-2,4,6-triol (5 g) in POCl$_3$ (30 ml) and 2,6-lutidine (15 ml) was heated to 90° C. for 3 hours. The reaction mixture was allowed to cool to room temperature and the volatiles were evaporated. Purification by column chromatography (ISCO, EtOAc/hexanes 1:10) provided the title compound (1.03 g) along with 2,4,5,6-tetrachloro pyrimidine. LCMS: 228 [M+1].

Intermediate 38

5,6-Dichloro-N-(5-isopropoxy-1H-pyrazol-3-yl)-3-nitropyridin-2-amine

The title compound was prepared using a procedure similar to the one described for the synthesis of Intermediate 7, using Intermediate 6 and Intermediate 7 as the starting materials. MS (electrospray): 333 (M+1) for C$_{11}$H$_{11}$Cl$_2$N$_5$O$_3$.

Intermediate 39

3-Chloro-N$^2$-[(1S)-1-(5-fluoropyridin-2-yl)ethyl]-N$^6$-(5-isopropoxy-1H-pyrazol-3-yl)-5-nitropyridine-2,6-diamine A mixture of 5,6-dichloro-N-(5-isopropoxy-1H-pyrazol-3-yl)-3-nitropyridin-2-amine (Intermediate 38, 0.75 g) and [(1S)-1-(5-fluoropyridin-2-yl)ethyl]amine hydrochloride (Intermediate 5, 0.50 g) in n-BuOH (20 mL) with diisopropylethylamine (3 mL) was stirred at 70° C. for 4 hours. The resulting mixture was diluted with ethyl acetate (20 mL), and washed with brine (10 mL×3). The organic layer was dried and concentrated. The resulting residue was separated by silica gel column (Hexane/Ethyl acetate) to yield 1.0 g of desired product. MS (electrospray): 436 (M+1) for $C_{18}H_{19}ClFN_7O_3$. $^1$H NMR (300 MHz, DMSO-d$_6$) δ ppm 12.0 (br 1H) 10.8 (br 1H) 8.60 (s, 1H) 8.30 (s, 3H) 7.80 (m, 1H) 7.40 (m, 1H) 6.00 (s, 1H) 5.50 (m, 1H) 4.50 (m, 1H) 1.60 (d, 3H) 1.30 (d, 6H).

Intermediate 40

2,3,6-Tri fluoro-5-nitropyridine

To a 3-neck, round-bottomed flask was added 2,3,6-trifluoropyridine (25 g, 0.19 mol) followed by the addition of red fuming nitric acid (210 mL, 4.7 mol). Sulfuric acid (150 mL, 2.8 mol) was added to this mixture slowly via an addition funnel, maintaining internal temperature below 40° C. The resulting solution was heated to 60° C. for 30 minutes and allowed to cool to room temperature after heating. This solution was then further cooled in an ice-water bath and inversely quenched into a 2-L Erlenmeyer flask containing a mixture of ice and water (700 mL, 1:1 ratio). The quenched solution was then transferred to a 2-L separatory funnel and partitioned with hexanes (600 mL). The aqueous layer was subsequently washed with hexanes (600 mL) and methylene chloride (600 mL). The combined organic layers were then dried over $Na_2SO_4$, filtered, and concentrated to provide the title compound as a light yellow liquid (19.2 g, 57% yield).
$^1$H NMR (CDCl$_3$) □ 8.74 (s, 1H).

Intermediate 41

5,6-Difluoro-N-(5-methyl-1H-pyrazol-3-yl)-3-nitropyridin-2-amine

To a solution of 2,3,6-trifluoro-5-nitropyridine (Intermediate 40, 1.0 g) in EtOH (20 ml) at 0° C., was added 5-methyl-1H-pyrazol-3-amine (550 mg) and DIPEA (2 ml). The resulting mixture was stirred at this temperature overnight. The title compound was collected via filtration (780 mg). LCMS: 377 [M+1].

Intermediate 42

3-Fluoro-N$^2$-[(1S)-1-(5-fluoropyrimidin-2-yl)ethyl]-methyl-1H-pyrazol-3-yl)-5-nitropyridine-2,6-diamine To a solution of 5,6-difluoro-N-(5-methyl-1H-pyrazol-3-yl)-3-nitropyridin-2-amine (Intermediate 41, 778 mg, 3.06 mmol) in n-BuOH (10 ml) was added the hydrochloride salt of [(1S)-1-(5-fluoropyrimidin-2-yl)ethyl]amine hydrochloride (554 mg, 3.06 mmol) and DIPEA (~1.1 ml). The resulting mixture was heated to 110° C. overnight. The resulting mixture was cooled to room temperature and the solvent was removed under reduced pressure to give a colored residue. Purification by column chromatography (Biotage, 50%→70% EtOAc/hexanes) afforded the title compound. LCMS: 378 [M+1].

Intermediate 43

6-Chloro-N-(5-methyl-1H)-pyrazol-3-yl)-3-nitropyridin-2-amine

The title compound was prepared using a procedure similar to the one described for the synthesis of Intermediate 9, using 2,6-dichloro-3-nitropyridine and 5-methyl-1H-pyrazol-3-amine as the starting materials. LCMS: 254 [M+1].

Intermediate 44

N$^6$-[(1S)-1-(5-Fluoropyrimidin-2-yl)ethyl]-N$^2$-(5-methyl-1H-pyrazol-3-yl)-3-nitropyridine-2,6-diamine The title compound was prepared using a procedure similar to the one described for the synthesis of Intermediate 8 using [(1S)-1-(5-fluoropyrimidin-2-yl)ethyl]amine hydrochloride (Intermediate 15) and 6-chloro-N-(5-methyl-1H)-pyrazol-3-yl)-3-nitropyridin-2-amine (Intermediate 43) as the starting materials. LCMS: 359 [M+1].

Intermediate 45

N$^6$-[(1S)-1-(5-Fluoropyrimidin-2-yl)ethyl]-N$^2$-(5-methyl-1H-pyrazol-3-yl)-3-nitropyridine-2,6-diamine The title compound was prepared using a procedure similar to the one described for the synthesis of Intermediate 8 using [(1S)-1-(5-fluoropyrimidin-2-yl)ethyl]amine hydrochloride (Intermediate 5) and 6-chloro-N-(5-methyl-1H)-pyrazol-3-yl)-3-nitropyridin-2-amine (Intermediate 43) as the starting materials. LCMS: 358 [M+1].

Intermediate 46

2-Chloro-N-(5-methyl-1H-pyrazol-3-yl)-5-nitropyrimidin-4-amine

The title compound was prepared using a procedure similar to the one described for the synthesis of Intermediate 30 using 2,6-dichloro-3-nitropyrimidine and 5-methyl-1H-pyrazol-3-amine as the starting materials. LCMS: 255 [M+1].

Intermediate 47

6-Chloro-N-(5-methyl-1H)-pyrazol-3-yl)-3-nitropyrimidin-2-amine

The title compound was prepared using a procedure similar to the one described for the synthesis of Intermediate 18, using [(1S)-1-(5-fluoropyridin-2-yl)ethyl]amine hydrochloride (Intermediate 5) and 6-chloro-N-(5-methyl-1H)-pyrazol-3-yl)-3-nitropyrimidin-2-amine (Intermediate 46) as the starting materials. LCMS: 359 [M+1].

Intermediate 48

Ethyl 2-chloro-6-[(5-methyl-1H-pyrazol-3-yl)amino]-5-nitropyrimidine-4-carboxylate The title compound was prepared using a procedure similar to the one described for the synthesis of Intermediate 30 using ethyl 2,6-dichloro-5-nitropyrimidine-4-carboxylate and 5-methyl-1H-pyrazol-3-amine as the starting materials. LCMS: 327 [M+1].

Intermediate 49

Ethyl 2-{[(1S)-1-(5-fluoropyrimidin-2-yl)ethyl]amino}-6-[(5-methyl-1H-pyrazol-3-yl)amino]-5-nitropyrimidine-4-carboxylate The title compound was prepared using a procedure similar to the one described for the synthesis of Intermediate 18 using

[(1S)-1-(5-fluoropyrimidin-2-yl)ethyl]amine hydrochloride (Intermediate 15) and ethyl 2-chloro-6-[(5-methyl-1H-pyrazol-3-yl)amino]-5-nitropyrimidine-4-carboxylate (Intermediate 48) as the starting materials. LCMS: 432 [M+1].

Intermediate 50

2-{[(1S)-1-(5-Fluoropyrimidin-2-yl)ethyl]amino}-6-[(5-methyl-1H-pyrazol-3-yl)amino]-5-nitropyrimidine-4-carboxylic acid To a solution of ethyl 2-{[(1S)-1-(5-fluoropyrimidin-2-yl)ethyl]amino}-6-[(5-methyl-1H-pyrazol-3-yl)amino]-5-nitropyrimidine-4-carboxylate (Intermediate 49, 2 mmol) in THF/MeOH (1:1 v/v, 10 ml) was added LiOH (0.42 g) in H$_2$O (1 ml) and the resulting mixture was stirred at ambient temperature overnight. The volatiles were evaporated under reduced pressure and the solid left was diluted with H2O. The aqueous layer was acidified with 1N HCl (aq) solution and extracted with EtOAc (3×). The combined organic layers were dried and evaporation gave the title compound (406 mg), used in the next step without further purification. LCMS: 402 [M−1].

Intermediate 51

N$^2$-[(1S)-1-(5-Fluoropyrimidin-2-yl)ethyl]-N$^4$-(5-methyl-1H-pyrazol-3-yl)-6-(morpholin-4-ylcarbonyl)-5-nitropyrimidine-2,4-diamine To a solution of 2-{[(1S)-1-(5-fluoropyrimidin-2-yl)ethyl]amino}-6-[(5-methyl-1H-pyrazol-3-yl)amino]-5-nitropyrimidine-4-carboxylic acid (Intermediate 50, 406 mg, ~1 mmol), in DMF (5 ml) were added DIPEA (~0.3 ml), HATU (456 mg) and morpholine (0.130 ml) at ambient temperature. The resulting mixture was stirred overnight. The mixture was diluted with H$_2$O and EtOAc and the aqueous layer was extracted with EtOAc. The combined organic layers were washed with brine, saturated NaHCO$_3$ (aq) solution, dried and evaporation of the volatiles under reduced pressure gave a colored residue. Purification by column chromatography (ISCO, 50%→70% EtOAc/hexanes) gave the title compound. LCMS: 473 [M+1].

Intermediate 52

2-Chloro-N-(5-methyl-1H-pyrazol-3-yl)-5-nitro-N-(tetrahydro-2H-pyran-4-yl)pyrimidine-4,6-diamine To a solution of 2,4,6-trichloro-5-nitro pyrimidine (Intermediate 37, 1 g, 4.4 mmol) in EtOH at −50° C. were added 5-methyl-1H-pyrazol-3-amine (255 mg) and DIPEA (1.6 ml) drop-wise. The resulting mixture was stirred at this temperature for 5 minutes whereupon 4-amino pyran (300 mg) was added. The resulting mixture was allowed to warm to ambient temperature for 4 hours. The mixture was diluted with H$_2$O and EtOAc and the aqueous layer was extracted with EtOAc. The combined organic layers were washed with brine, saturated NaHCO$_3$ (aq) solution, dried and evaporation of the volatiles under reduced pressure gave a colored residue. Purification by Gilson (MeCN/H$_2$O, 5%→95%, 15 minutes) gave the title compound (120 mg). LCMS: 354 [M+1].

Intermediate 53

N$^2$-[(1S)-1-(5-Fluoropyridin-2-yl)ethyl]-N$^4$-(5-methyl-1H-pyrazol-3-yl)-5-nitro-N$^6$-(tetrahydro-2H-pyran-4-yl)pyrimidine-2,4,6-triamine The title compound was prepared using a procedure similar to the one described for the synthesis of Intermediate 18 using [(1S)-1-(5-fluoropyridin-2-yl)ethyl]amine hydrochloride (Intermediate 5) and 2-chloro-N-(5-methyl-1H-pyrazol-3-yl)-5-nitro-N-(tetrahydro-2H-pyran-4-yl)pyrimidine-4,6-diamine (Intermediate 52) as the starting materials. LCMS: 458 [M+1].

Intermediate 54

2-Chloro-6-methoxy-N-(5-methyl-1H-pyrazol-3-yl)-5-nitropyrimidin-4-amine

The title compound was prepared using a procedure similar to the one described for the synthesis of Intermediate 18 using 2,4,6-trichloro-5-nitropyrimidine (Intermediate 37), 5-methyl-1H-pyrazol-3-amine and sodium methoxide as the starting materials. LCMS: 285 [M+1].

Intermediate 55

N$^2$-[(1S)-1-(5-Fluoropyridin-2-yl)ethyl]-6-methoxy-N$^4$-(5-methyl-1H-pyrazol-3-yl)-5-nitropyrimidine-2,4-diamine The title compound was prepared using a procedure similar to the one described for the synthesis of Intermediate 18 using [(1S)-1-(5-fluoropyridin-2-yl)ethyl]amine hydrochloride (Intermediate 5) and 2-chloro-6-methoxy-N-(5-methyl-1H-pyrazol-3-yl)-5-nitropyrimidin-4-amine (Intermediate 54) as the starting materials. LCMS: 389 [M+1].

Intermediate 56

4,6-Dichloro-2-(methylthio)-5-nitropyrimidine

To 50 ml of absolute EtOH was added Na metal (1 g) in small portions and the resulting mixture was stirred for 10 minutes after the addition of Na had finished. Thiourea (1.6 g) and diethyl nitromalonate (2.0 g) were added, whereupon a yellow suspension was observed. This suspension was heated to reflux for 3 hours and subsequently was allowed to cool to ambient temperature. The mixture was acidified with caution to pH~2 with 5N HCl (aq) whereupon a precipitate was observed. The precipitate was collected by filtration, washed with EtOH, H$_2$O and dried overnight in a vacuum oven. The solid (2.15 g) was dissolved in a solution of 2.5N NaOH (16 ml) and the resulting mixture was stirred for 20 minutes at ambient temperature. Methyl iodide (1.6 g) was added drop-wise via a syringe and a colored suspension was observed upon completion of the addition. The mixture was acidified with glacial AcOH, and the derived precipitate was collected via filtration, washed with H$_2$O and dried in a vacuum oven overnight (1.2 g). The solid (1.2 g) was added slowly to a mixture of POCl$_3$ (30 ml) and 2,6-lutidine (15 ml) and the resulting mixture was heated to 80° C. for 1 hour. The reaction mixture was allowed to cool to room temperature and the volatiles were evaporated. Purification by column chromatography (EtOAc/hexanes 1:10) provided the title compound (1.0 g). LCMS: 240 [M+1].

Intermediate 57

N-(5-Methyl-1H-pyrazol-3-yl)-2-(methylthio)-6-morpholin-4-yl-5-nitropyrimidin-4-amine To a solution of 4,6-dichloro-2-(methylthio)-5-nitropyrimidine (Intermediate 56, 820 mg) in THF at 0° C. were added 5-methyl-1H-pyrazol-3-amine (350 mg) and DIPEA (1.6 ml) drop-wise. The resulting mixture was stirred at this temperature for 3 hours whereupon morpholine (1 ml) was added. The resulting mixture was allowed to warm to ambient temperature over 10 hours. The mixture was diluted with $H_2O$ and EtOAc and the aqueous layer was extracted with EtOAc. The combined organic layers were washed with brine, saturated $NaHCO_3$ (aq) solution, dried and evaporation of the volatiles under reduced pressure gave a colored residue. Purification by column chromatography (50% EtOAc/hexanes) gave the title compound (820 mg). LCMS: 352 [M+1].

Intermediate 58

$N^2$-[(1S)-1-(5-Fluoropyridin-2-yl)ethyl]-$N^4$-(5-methyl-1H-pyrazol-3-yl)-6-morpholin-4-yl-5-nitropyrimidine-2,4-diamine To a solution of N-(5-methyl-1H-pyrazol-3-yl)-2-(methylthio)-6-morpholin-4-yl-5-nitropyrimidin-4-amine (Intermediate 57, 118 mg) in MeOH (2 ml) and DCM (2 ml) were added Oxone® (302 mg) and $NaHCO_3$ (56 mg) and the resulting mixture was stirred at ambient temperature for 16 hours. [(1S)-1-(5-fluoropyridin-2-yl)ethyl]amine (Intermediate 8, 250 mg) and DIPEA (3 ml) were added and the resulting mixture was stirred at ambient temperature for 3 hours. The mixture was diluted with $H_2O$ and EtOAc and the aqueous layer was extracted with EtOAc (4x). The combined organic layers were washed with brine, saturated $NaHCO_3$ (aq) solution, dried and evaporation of the volatiles under reduced pressure gave a colored residue. Purification by column chromatography (60% EtOAc/hexanes) gave the title compound (220 mg). LCMS: 444 [M+1].

Intermediate 59

$N^2$-(5-Ethoxy-1H-pyrazol-3-yl)-$N^6$-[(1S)-1-(5-fluoropyridin-2-yl)propyl]-3-nitropyridine-2,6-diamine The title compound was prepared using a procedure similar to the one described for the synthesis of Intermediate 28 using 6-chloro-N-(5-ethoxy-1H-pyrazol-3-yl)-3-nitropyridin-2-amine (Intermediate 26) and [(1S)-1-(5-fluoropyridin-2-yl)propyl]amine (Intermediate 35) as the starting materials. LCMS: 402 [M+1]. $^1$H NMR (400 MHz, DMSO-d6) δ 12.00 (s, 1H), 11.00 (s, 1H), 8.80 (s, 1H), 8.50 (s, 1H), 8.10 (d, 1H), 7.60 (m, 1H), 7.20 (m, 1H), 6.30 (m, 1H), 5.80 (s, 1H), 5.00 (m, 1H), 4.10 (q, 2H), 2.00 (m, 2H), 1.40 (d, 3H), 1.10 (t, 3H).

Intermediate 60

Ethyl 2-{[(1S)-1-(5-fluoropyridin-2-yl)ethyl]amino}-6-[(5-methyl-1H-pyrazol-3-yl)amino]-5-nitropyrimidine-4-carboxylate The title compound was prepared using a procedure analogous to the one described for Intermediate 29, using [(1S)-1-(5-fluoropyridin-2-yl)ethyl]amine hydrochloride (Intermediate 5) and ethyl 2-chloro-6-[(5-methyl-1H-pyrazol-3-yl)amino]-5-nitropyrimidine-4-carboxylate (Intermediate 48) as the starting materials. LCMS: 431 [M+1].

Example 1

N-[(1S)-1-(5-fluoropyridin-2-yl)ethyl]-3-(5-isopropoxy-1H-pyrazol-3-yl)-3H-imidazo[4,5-b]pyridin-5-amine

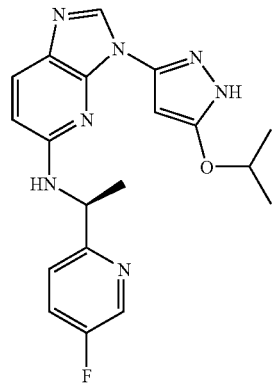 [SMILES: CC(C)Oc1cc(-n2cnc3ccc(N[C@@H](C)c4ccc(F)cn4)nc32)n[nH]1]

$N^6$-[(1S)-1-(5-fluoropyridin-2-yl)ethyl]-$N^2$-(5-isopropoxy-1H-pyrazol-3-yl)-3-nitropyridine-2,6-diamine (Intermediate 8, 0.5 g) was dissolved into ethanol (20 mL) with Pd—C (60 mg) and a hydrogen inlet. The mixture was stirred at room temperature until no starting material was detected with TLC or LCMS. Formamidine acetate (0.5 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.29 g of the title compound. MS (electrospray): 382 (M+1) for $C_{19}H_{20}FN_7O$. $^1$H NMR (300 MHz, $CD_3OD$) δ ppm 8.45 (s, 1H) 8.35 (s, 1H) 7.75 (d, 1H) 7.50 (s, 1H) 6.70 (d, 1H) 6.00 (s, 1H) 5.10 (m, 1H) 4.50 (m, 1H) 1.55 (d, 3H) 1.35 (d, 6H).

Example 2

3-(5-Cyclopropyl-1H-pyrazol-3-yl)-N-[(1S)-1-(5-fluoropyridin-2-yl)ethyl]-3H-imidazo[4,5-b]pyridin-5-amine

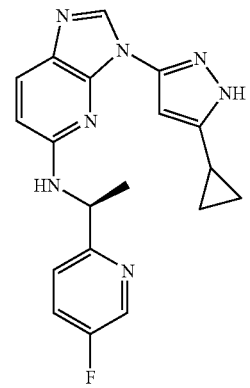 [SMILES: C[C@H](Nc1ccc2ncn(-c3cc(C4CC4)[nH]n3)c2n1)c1ccc(F)cn1]

$N^2$-(5-cyclopropyl-1H-pyrazol-3-yl)-$N^6$-[(1S)-1-(5-fluoropyridin-2-yl)ethyl]-3-nitropyridine-2,6-diamine (Intermediate 10, 0.4 g) was dissolved into ethanol (20 mL) with Pd—C (60 mg) and a hydrogen inlet. The mixture was stirred at room temperature until no starting material was detected with TLC or LCMS. Formamidine acetate (0.5 g) was added to the filtrate after the filtration of resulting mixture. The mixture was stirred at 95° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.16 g of the title compound. MS (electrospray): 364 (M+1) for $C_{19}H_{18}FN_7$. $^1$H NMR (300 MHz, CD$_3$OD) δ ppm 8.45 (s, 1H) 8.30 (s, 1H) 7.70 (d, 1H) 7.50 (d, 1H) 6.70 (d, 1H) 6.20 (s, 1H) 5.10 (dd, 1H) 2.00 (m, 1H) 1.55 (d, 3H) 1.00 (m, 2H) 0.80 (m, 2H).

Example 3

3-(5-Cyclopropyl-1H-pyrazol-3-yl)-N-[(1S)-1-(5-fluoropyrimidin-2-yl)ethyl]-3H-imidazo[4,5-b]pyridin-5-amine

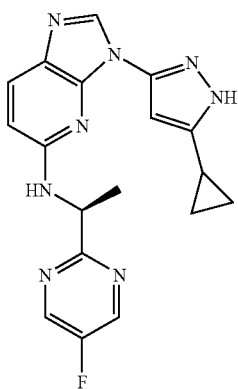 [SMILES: C[C@H](Nc1ccc2ncn(-c3cc(C4CC4)[nH]n3)c2n1)c1ncc(F)cn1]

N$^2$-(5-cyclopropyl-1H-pyrazol-3-yl)-N$^6$-[(1S)-1-(5-fluoropyrimidin-2-yl)ethyl]-3-nitropyridine-2,6-diamine (Intermediate 16, 0.45 g) was dissolved into ethanol (20 mL) with Pd—C (60 mg) and a hydrogen inlet. The mixture was stirred at room temperature until no starting material was detected with TLC or LCMS. Formylamidine acetate (0.5 g) was added to the filtrate after the filtration of resulting mixture. The mixture was stirred at 95° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.08 g of the title compound. MS (electrospray): 365 (M+1) for $C_{18}H_{17}FN_8$. $^1$H NMR (300 MHz, CD$_3$OD) δ ppm 8.70 (s, 2H) 8.30 (s, 1H) 7.70 (d, 1H) 6.70 (d, 1H) 6.50 (s, 1H) 5.30 (dd, 1H) 2.00 (m, 1H) 1.60 (d, 3H) 1.10 (m, 2H) 0.90 (m, 2H).

Example 4

9-(5-Cyclopropyl-1H-pyrazol-3-yl)-N-[(1S)-1-(5-fluoropyrimidin-2-yl)ethyl]-9H-purin-2-amine

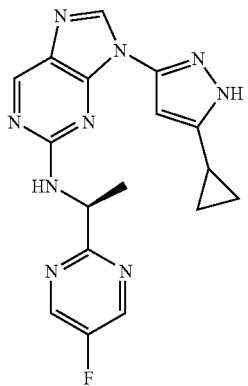 [SMILES: C[C@H](Nc1ncc2ncn(-c3cc(C4CC4)[nH]n3)c2n1)c1ncc(F)cn1]

N$^4$-(5-cyclopropyl-1H-pyrazol-3-yl)-N$^2$-[(1S)-1-(5-fluoropyrimidin-2-yl)ethyl]-5-nitropyrimidine-2,4-diamine (Intermediate 18, 0.25 g) was dissolved into ethanol (20 mL) with Pd—C (40 mg) and a hydrogen inlet. The mixture was stirred at room temperature until no starting material was detected with TLC or LCMS. Formamidine acetate (0.5 g) was added to the filtrate after the filtration of resulting mixture. The mixture was stirred at 95° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.013 g of the title compound. MS (electrospray): 366 (M+1) for $C_{17}H_{17}FN_9$. $^1$H NMR (300 MHz, CD$_3$OD) δ ppm 8.70 (s, 2H) 8.65 (s, 1H) 8.40 (s, 1H) 6.40 (d, 1H) 5.30 (dd, 1H) 2.00 (m, 1H) 1.65 (d, 3H) 1.10 (m, 2H) 0.90 (m, 2H).

Example 5

9-(5-Cyclopropyl-1H-pyrazol-3-yl)-N-[(1S)-1-(5-fluoropyridin-2-yl)ethyl]-9H-purin-2-amine

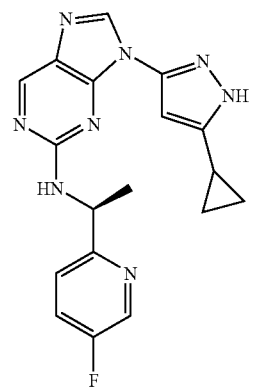 [SMILES: C[C@H](Nc1ncc2ncn(-c3cc(C4CC4)[nH]n3)c2n1)c1ccc(F)cn1]

N$^4$-(5-cyclopropyl-1H-pyrazol-3-yl)-N$^2$-[(1S)-1-(5-fluoropyridin-2-yl)ethyl]-5-nitropyrimidine-2,4-diamine (Intermediate 19, 0.25 g) was dissolved into ethanol (20 mL) with Pd—C (40 mg) and a hydrogen inlet. The mixture was stirred at room temperature until no starting material was detected with TLC or LCMS. Formamidine acetate (0.5 g) was added to the filtrate after the filtration of resulting mixture. The mixture was stirred at 95° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.03 g of the title compound. MS (electrospray): 365 (M+1) for $C_{18}H_{17}FN_8$. $^1$H NMR (300 MHz, CD$_3$OD) δ ppm 8.70 (s, 2H) 8.55 (s, 1H) 8.50 (s, 1H) 7.50 (d, 2H) 6.30 (br, 1H) 5.20 (dd, 1H) 2.00 (m, 1H) 1.65 (d, 3H) 1.10 (m, 2H) 0.90 (m, 2H).

Example 6

N-[(1S)-1-(5-Fluoropyrimidin-2-yl)ethyl]-3-(5-isopropoxy-1H-pyrazol-3-yl)-3H-imidazo[4,5-b]pyridin-5-amine

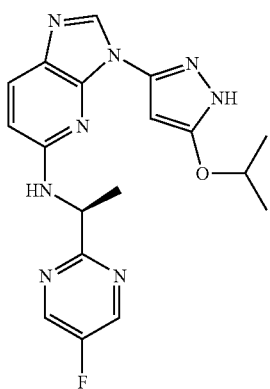 [SMILES: CC(C)Oc1cc(-n2cnc3ccc(N[C@@H](C)c4ncc(F)cn4)nc32)n[nH]1]

$N^6$-[(1S)-1-(5-fluoropyrimidin-2-yl)ethyl]-$N^2$-(5-isopropoxy-1H-pyrazol-3-yl)-3-nitropyridine-2,6-diamine (Intermediate 20, 0.5 g) was dissolved into ethanol (20 mL) with Pd—C (60 mg) and a hydrogen inlet. The mixture was stirred at room temperature until no starting material was detected with TLC or LCMS. Formamidine acetate (0.5 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.29 g of the title compound. MS (electrospray): 383 (M+1) for $C_{18}H_{19}FN_8O$. $^1$H NMR (300 MHz, CD$_3$OD) δ ppm 8.75 (s, 2H) 8.35 (s, 1H) 7.80 (d, 1H) 6.80 (d, 1H) 6.30 (s, 1H) 5.30 (m, 1H) 4.70 (m, 1H) 1.55 (d, 3H) 1.35 (d, 6H).

Example 7

(2R)-2-(5-Fluoropyridin-2-yl)-2-{[3-(5-isopropoxy-1H-pyrazol-3-yl)-3H-imidazo[4,5-b]pyridin-5-yl]amino}ethanol

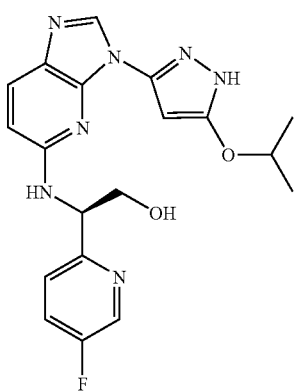

(2R)-2-(5-fluoropyridin-2-yl)-2-({6-[(5-isopropoxy-1H-pyrazol-3-yl)amino]-5-nitropyridin-2-yl}amino)ethanol (Intermediate 24, 0.45 g) was dissolved into ethanol (20 mL) with Pd—C (90 mg) and a hydrogen inlet. The mixture was stirred at room temperature until no starting material was detected with TLC or LCMS. Formamidine acetate (0.5 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by a silica gel column (Ethyl acetate/MeOH) to afford 0.075 g of the title compound. MS (electrospray): 398 (M+1) for $C_{19}H_{20}FN_7O_2$. $^1$H NMR (300 MHz, CD$_3$OD) δ ppm 8.50 (d, 1H) 8.30 (s, 1H) 7.80 (d, 1H) 7.50 (dd, 1H) 6.70 (d, 1H) 6.05 (s, 1H) 5.20 (m, 1H) 4.65 (m, 1H) 4.00 (m, 2H), 1.55-1.35 (m, 6H).

Example 8

(2R)-2-{[3-(5-Ethoxy-1H-pyrazol-3-yl)-3H-imidazo[4,5-b]pyridin-5-yl]amino}-2-(5-fluoropyridin-2-yl)ethanol

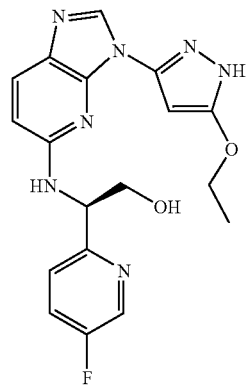 [SMILES: CCOc1cc(-n2cnc3ccc(N[C@@H](CO)c4ccc(F)cn4)nc32)n[nH]1]

(2R)-2-({6-[(5-ethoxy-1H-pyrazol-3-yl)amino]-5-nitropyridin-2-yl}amino)-2-(5-fluoropyridin-2-yl)ethanol (Intermediate 27, 0.2 g) was dissolved into ethanol (20 mL) with Pd—C (50 mg) and a hydrogen inlet. The mixture was stirred at room temperature until no starting material was detected with TLC or LCMS. Formylamidine acetate (0.5 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.06 g of the title compound MS (electrospray): 384 (M+1) for $C_{18}H_{18}FN_7O_2$. $^1$H NMR (300 MHz, CD$_3$OD) δ ppm 8.20 (d, 1H) 8.15 (s, 1H) 7.50 (d, 1H) 7.30 (dd, 1H) 6.40 (d, 1H) 5.85 (s, 1H) 5.00 (m, 1H) 4.00 (d, 2H) 3.80 (m, 2H) 1.00 (t, 3H).

Example 9

3-(5-Ethoxy-1H-pyrazol-3-yl)-N-[(1S)-1-(5-fluoro-pyrimidin-2-yl)ethyl]-3H-imidazo[4,5-b]pyridin-5-amine

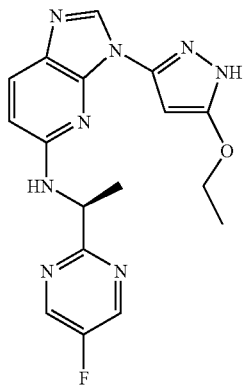 [SMILES: CCOc1cc(-n2cnc3ccc(N[C@@H](C)c4ncc(F)cn4)nc32)n[nH]1]

$N^2$-(5-Ethoxy-1H-pyrazol-3-yl)-$N^6$-[(1S)-1-(5-fluoropyrimidin-2-yl)ethyl]-3-nitropyridine-2,6-diamine (Intermediate 28, 0.3 g) was dissolved into ethanol (20 mL) with Pd—C (90 mg) and a hydrogen inlet. The mixture was stirred at room temperature until no starting material was detected with TLC or LCMS. Formylamidine acetate (0.5 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.034 g of the title compound. MS (electrospray): 369 (M+1) for $C_{17}H_{17}FN_8O$. $^1H$ NMR (300 MHz, $CD_3OD$) δ ppm 8.70 (s, 2H) 8.30 (s, 1H) 7.80 (d, 1H) 6.80 (d, 1H) 6.30 (s, 1H) 5.40 (m, 1H) 4.30 (q, 2H) 1.70 (d, 3H) 1.55 (t, 3H).

Example 10

3-(5-Ethoxy-1H-pyrazol-3-yl)-N-[(1S)-1-(5-fluoro-pyrimidin-2-yl)ethyl]-3H-imidazo[4,5-b]pyridin-5-amine

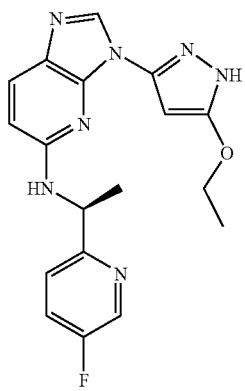 [SMILES: CCOc1cc(-n2cnc3ccc(N[C@@H](C)c4ccc(F)cn4)nc32)n[nH]1]

$N^2$-(5-Ethoxy-1H-pyrazol-3-yl)-$N^6$-[(1S)-1-(5-fluoropyridin-2-yl)ethyl]-3-nitropyridine-2,6-diamine (Intermediate 29, 0.3 g) was dissolved into ethanol (20 mL) with Pd—C (90 mg) and a hydrogen inlet. The mixture was stirred at room temperature until no starting material was detected with TLC or LCMS. Formamidine acetate (0.5 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.034 g desired product. MS (electrospray): 368 (M+1) for $C_{18}H_{18}FN_7O$. $^1H$ NMR (300 MHz, $CD_3OD$) δ ppm 8.30 (s, 1H) 8.20 (s, 1H) 7.70 (d, 1H) 7.40 (d, 1H) 6.60 (d, 1H) 5.90 (s, 1H) 5.10 (m, 1H) 4.10 (q, 2H) 1.50 (d, 3H) 1.40 (t, 3H).

Example 11

N-[(1S)-1-(5-Fluoropyridin-2-yl)ethyl]-9-(5-isopropoxy-1H-pyrazol-3-yl)-9H-purin-2-amine

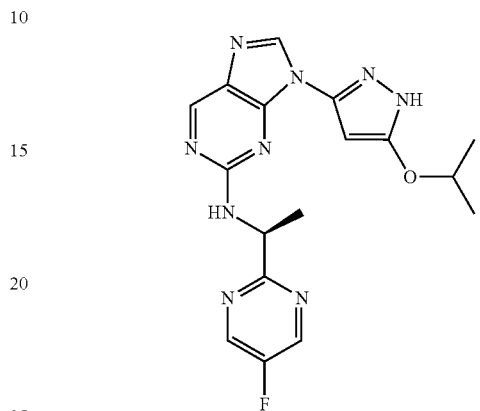

$N^2$-[(1S)-1-(5-fluoropyridin-2-yl)ethyl]-$N^4$-(5-isopropoxy-1H-pyrazol-3-yl)-5-nitropyrimidine-2,4-diamine (Intermediate 31, 1.0 g) was dissolved into ethanol (20 mL) with Pd—C (150 mg) and a hydrogen inlet. The mixture was stirred at room temperature until no starting material was detected with TLC or LCMS. Formamidine acetate (1.0 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.7 g desired product. MS (electrospray): 383 (M+1) for $C_{18}H_{19}FN_8O$. $^1H$ NMR (300 MHz, $CD_3OD$) δ ppm 8.70 (s, 1H) 8.40 (m, 2H) 7.50 (dd, 2H) 6.00 (s, 1H) 5.20 (m, 1H) 4.20 (m, 1H) 1.50 (d, 3H) 1.40 (d, 6H).

Example 12

N-[(1S)-1-(5-Fluoropyrimidin-2-yl)ethyl]-9-(5-isopropoxy-1H-pyrazol-3-yl)-9H-purin-2-amine

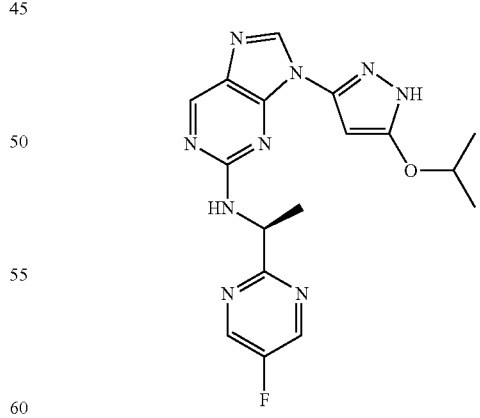

$N^2$-[(1S)-1-(5-fluoropyrimidin-2-yl)ethyl]-$N^4$-(5-isopropoxy-1H-pyrazol-3-yl)-5-nitropyrimidine-2,4-diamine (Intermediate 32, 0.2 g) was dissolved into ethanol (20 mL) with Pd—C (40 mg) and a hydrogen inlet. The mixture was stirred at room temperature until no starting material was detected with TLC or LCMS. Formamidine acetate (0.5 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.08 g desired product. MS (electrospray): 384 (M+1) for $C_{17}H_{18}FN_9O$. $^1H$ NMR (300 MHz, $CD_3OD$) δ ppm 8.70 (s, 2H) 8.60 (s, 1H) 8.40 (s, 1H) 6.20 (s, 1H) 5.30 (m, 1H) 4.60 (m, 1H) 1.60 (d, 3H) 1.50 (d, 6H).

Example 13

N-[(1S)-1-(5-Fluoropyridin-2-yl)propyl]-3-(5-isopropoxy-1H-pyrazol-3-yl)-3H-imidazo[4,5-b]pyridin-5-amine

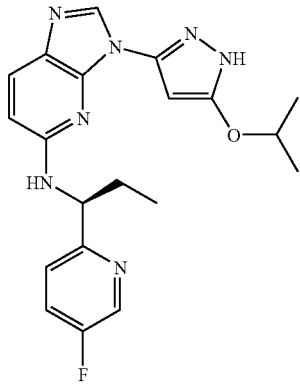 [SMILES: CC[C@H](Nc1ccc2ncn(-c3cc(OC(C)C)[nH]n3)c2n1)c1ccc(F)cn1]

$N^6$-[(1S)-1-(5-fluoropyridin-2-yl)propyl]-$N^2$-(5-isopropoxy-1H-pyrazol-3-yl)-3-nitropyridine-2,6-diamine (Intermediate 36, 0.45 g) was dissolved into ethanol (20 mL) with Pd—C (150 mg) and a hydrogen inlet. The mixture was stirred at room temperature until no starting material was detected with TLC or LCMS. Formamidine acetate (0.5 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.12 g desired product. MS (electrospray): 396 (M+1) for $C_{20}H_{22}FN_7O$. $^1H$ NMR (300 MHz, $CD_3OD$) δ ppm 8.40 (s, 1H) 8.30 (s, 1H) 7.70 (d, 1H) 7.50 (m 2H) 6.70 (d, 1H) 6.10 (s, 1H) 5.00 (m, 1H) 4.40 (m, 1H) 2.00 (m, 2H) 1.40 (d, 6H).

Example 14

6-Chloro-N-[(1S)-1-(5-fluoropyridin-2-yl)ethyl]-3-(5-isopropoxy-1H-pyrazol-3-yl)-3H-imidazo[4,5-b]pyridin-5-amine

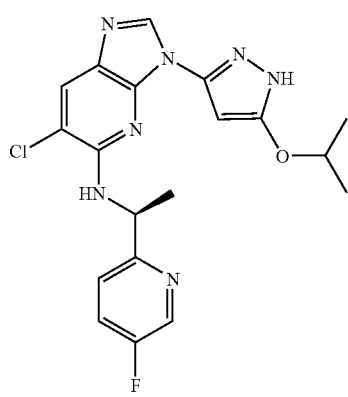 [SMILES: CC(C)Oc1cc(-n2cnc3cc(Cl)c(N[C@@H](C)c4ccc(F)cn4)nc32)n[nH]1]

3-Chloro-$N^2$-[(1S)-1-(5-fluoropyridin-2-yl)ethyl]-$N^6$-(5-isopropoxy-1H-pyrazol-3-yl)-5-nitropyridine-2,6-diamine (Intermediate 39, 0.5 g) was dissolved into ethanol (20 mL) with Pd—C (150 mg) and a hydrogen inlet. The mixture was stirred at room temperature until no starting material was detected with TLC or LCMS. Formylamidine acetate (0.5 g) was added to the filtrate after the filtration of resulting mixture. The mixture was stirred at 85° C. for 4 hours. Ethyl acetate (40 mL) was added into the resulting mixture, and brine (10 mL×3) was used to wash the organic layer. The organic layer was dried and concentrated. The resulting residue was separated by silica gel column (Ethyl acetate/MeOH) to afford 0.12 g desired product. MS (electrospray): 416 (M+1) for $C_{19}H_{19}ClFN_7O$. $^1H$ NMR (300 MHz, $CD_3OD$) δ ppm 8.40 (s, 1H) 8.30 (s, 1H) 7.90 (d, 1H) 7.50 (m 2H) 6.70 (d, 1H) 6.00 (s, 1H) 5.40 (m, 1H) 4.60 (m, 1H) 1.60 (d, 3H) 1.40 (d, 6H).

Example 15

6-Fluoro-N-[(1S)-1-(5-fluoropyrimidin-2-yl)ethyl]-3-(5-methyl-1H-pyrazol-3-yl)-3H-imidazo[4,5-b]pyridin-5-amine

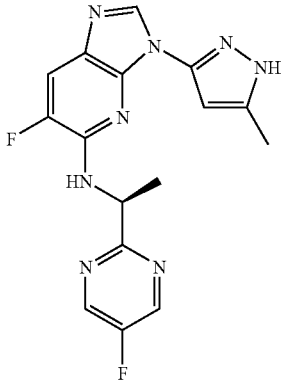 [SMILES: Cc1cc(-n2cnc3cc(F)c(N[C@@H](C)c4ncc(F)cn4)nc32)n[nH]1]

To a solution of 3-fluoro-$N^2$-[(1S)-1-(5-fluoropyrimidin-2-yl)ethyl]-$N^6$-(5-methyl-1H-pyrazol-3-yl)-5-nitropyridine-2,6-diamine (Intermediate 42, 3.05 mmol) in EtOH (5 ml) were added $SnCl_2.2H_2O$ (1.74 g, 9.18 mmol) and triethyl orthoformate (0.652 ml). The resulting solution was heated to 70° C. overnight. The mixture was allowed to cool to room temperature and filtered through Celite® and washed with EtOAc. Evaporation of the volatiles under reduced pressure gave a colored residue that was purified by Gilson (5%→95% MeCN/$H_2O$) to give the title compound. LC-MS: 357 [M+1]. $^1H$ NMR δ 2.01 (d, 3H) 2.34 (s, 3H) 6.46-6.55 (m, 1H) 8.20 (s, 1H) 8.72 (s, 1H) 8.87 (s, 2H) 9.72 (s, 1H) 9.86 (s, 1H).

Example 16

N-[(1S)-1-(5-Fluoropyrimidin-2-yl)ethyl]-3-(5-methyl-1H-pyrazol-3-yl)-3H-imidazo[4,5-b]pyridin-5-amine

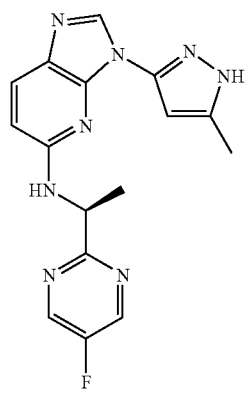 [SMILES: Cc1cc(-n2cnc3ccc(N[C@@H](C)c4ncc(F)cn4)nc32)n[nH]1]

The title compound was prepared using a procedure similar to the one described for the synthesis of Example 15 using N$^6$-[(1S)-1-(5-fluoropyrimidin-2-yl)ethyl]-N$^2$-(5-methyl-1H-pyrazol-3-yl)-3-nitropyridine-2,6-diamine (Intermediate 44) as the starting material. LCMS: 339 [M+1]. $^1$H NMR δ 1.46 (d, 3H) 2.28 (s, 3H) 5.08 (s, 1H) 6.33 (s, 1H) 6.65 (s, 1H) 7.71 (s, 1H) 8.77 (s, 2H).

Example 17

N-[(1S)-1-(5-Fluoropyridin-2-yl)ethyl]-3-(5-methyl-1H-pyrazol-3-yl)-3H-imidazo[4,5-b]pyridin-5-amine

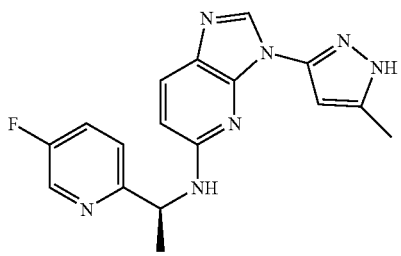 [SMILES: Cc1cc(-n2cnc3ccc(N[C@@H](C)c4ccc(F)cn4)nc32)n[nH]1]

The title compound was prepared using a procedure similar to the one described for the synthesis of Example 15 using N$^6$-[(1S)-1-(5-fluoropyridin-2-yl)ethyl]-N$^2$-(5-methyl-1H-pyrazol-3-yl)-3-nitropyridine-2,6-diamine (Intermediate 45) as the starting material. LCMS: 338 [M+1]. $^1$H NMR (500 MHz, CDCl$_3$) δ 1.58 (d, 3H) 2.40 (s, 3H) 5.05-5.17 (m, 1H) 5.45 (s, 1H) 6.43 (d, 1H) 6.53 (1H, s) 7.35 (m, 2H), 7.81 (1H, d) 8.41 (s, 1H) 8.6 (br s, 1H).

Example 18

N-[(1S)-1-(5-Fluoropyridin-2-yl)ethyl]-9-(5-methyl-1H-pyrazol-3-yl)-9H-purin-2-amine

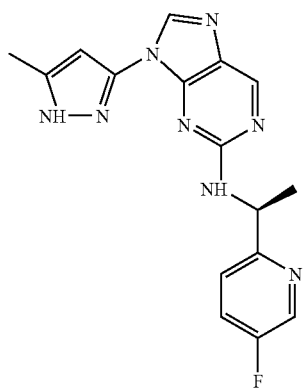 [SMILES: Cc1cc(-n2cnc3cnc(N[C@@H](C)c4ccc(F)cn4)nc32)n[nH]1]

The title compound was prepared using a procedure similar to the one described for the synthesis of Example 15 using 6-chloro-N-(5-methyl-1H)-pyrazol-3-yl)-3-nitropyrimidin-2-amine (Intermediate 47) as the starting material. LCMS: 339 [M+1]. $^1$H NMR (500 MHz, CDCl$_3$) 1.62 (d, 3H) 2.41 (s, 3H) 5.23-5.26 (m, 1H) 6.094 (s, 1H) 6.52 (s, 1H) 7.41-7.32 (m, 2H) 8.26 (d, 1H) 8.34 (s, 1H) 8.45 (d, 1H) 8.73 (s, 1H).

Example 19

N-[(1S)-1-(5-Fluoropyrimidin-2-yl)ethyl]-9-(5-methyl-1H-pyrazol-3-yl)-6-(morpholin-4-ylcarbonyl)-9H-purin-2-amine

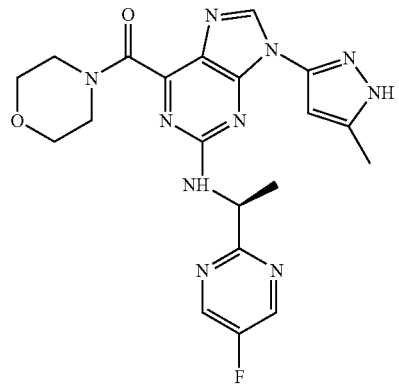 [SMILES: Cc1cc(-n2cnc3c(C(=O)N4CCOCC4)nc(N[C@@H](C)c4ncc(F)cn4)nc32)n[nH]1]

The title compound was prepared using a procedure similar to the one described for the synthesis of Example 4 using N$^2$-[(1S)-1-(5-fluoropyrimidin-2-yl)ethyl]-N$^4$-(5-methyl-1H-pyrazol-3-yl)-6-(morpholin-4-ylcarbonyl)-5-nitropyrimidine-2,4-diamine (Intermediate 51) as the starting material. LCMS: 453 [M+1]. $^1$H NMR δ 1.54 (d, 3H) 2.09 (s, 3H) 3.18-3.70 (m, 8H) 4.97-5.29 (m, 1H) 6.25 (s, 1H) 8.45 (s, 1H) 8.84 (s, 2H) 12.69 (s, 1H).

Example 20

N$^2$-[(1S)-1-(5-Fluoropyridin-2-yl)ethyl]-9-(5-methyl-1H-pyrazol-3-yl)-N$^6$-(tetrahydro-2H-pyran-4-yl)-9H-purine-2,6-diamine

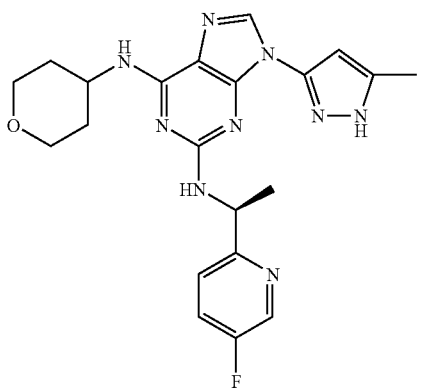 [SMILES: Cc1cc(-n2cnc3c(NC4CCOCC4)nc(N[C@@H](C)c4ccc(F)cn4)nc32)n[nH]1]

The title compound was prepared using a procedure similar to the one described for the synthesis of Example 4 using N$^2$-[(1S)-1-(5-fluoropyridin-2-yl)ethyl]-N$^4$-(5-methyl-1H-pyrazol-3-yl)-5-nitro-N$^6$-(tetrahydro-2H-pyran-4-yl)pyrimidine-2,4,6-triamine (Intermediate 53) as the starting material. LCMS: 438 [M+1]. $^1$H NMR (MeOD) δ 1.74-2.02 (m, 7H) 2.31 (s, 3H) 3.60 (s, 5H) 5.05-5.41 (m, 1H) 6.34 (s, 1H) 7.47-7.99 (m, 2H) 8.20 (s, 1H) 8.49 (s, 1H).

Example 21

N-[(1S)-1-(5-Fluoropyridin-2-yl)ethyl]-6-methoxy-9-(5-methyl-1H-pyrazol-3-yl)-9H-purin-2-amine

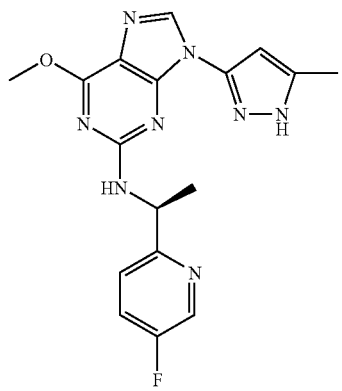

The title compound was prepared using a procedure similar to the one described for the synthesis of Example 4 using $N^2$-[(1S)-1-(5-fluoropyridin-2-yl)ethyl]-6-methoxy-$N^4$-(5-methyl-1H-pyrazol-3-yl)-5-nitropyrimidine-2,4-diamine (Intermediate 55) as the starting material. LCMS: 369 [M+1]. $^1$H NMR (MeOD) δ 1.67 (d, 3H) 2.44 (s, 3H) 3.63 (s, 3H) 5.08-5.49 (m, 1H) 6.44 (s, 1H) 7.91-8.10 (m, 1H) 8.13-8.36 (m, 1H) 8.77 (s, 1H) 9.33 (s, 1H).

Example 22

N-[(1S)-1-(5-Fluoropyridin-2-yl)ethyl]-9-(5-methyl-1H-pyrazol-3-yl)-6-morpholin-4-yl-9H-purin-2-amine

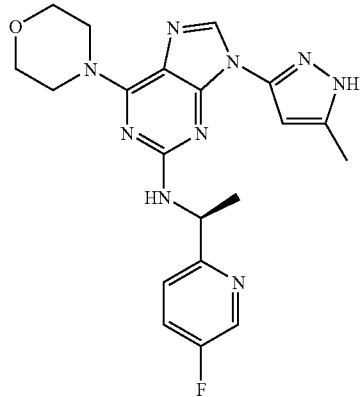 [SMILES: Cc1cc(-n2cnc3c(N4CCOCC4)nc(N[C@@H](C)c4ccc(F)cn4)nc32)n[nH]1]

The title compound was prepared using a procedure similar to the one described for the synthesis of Example 15 using $N^2$-[(1S)-1-(5-fluoropyridin-2-yl)ethyl]-$N^4$-(5-methyl-1H-pyrazol-3-yl)-6-morpholin-4-yl-5-nitropyrimidine-2,4-diamine (Intermediate 58) as the starting material. LCMS: 424 [M+1]. $^1$H NMR (500 MHz, CDCl$_3$) δ 1.54 (d, 3H) 2.31 (s, 3H) 3.72-3.74 (m, 4H) 4.15-4.20 (m, 4H) 5.12-5.17 (m, 1H) 6.44 (s, 1H) 7.24-7.36 (m, 2H) 7.95 (s, 1H) 8.38 (d, 1H).

Example 23

3-(5-Ethoxy-1H-pyrazol-3-yl)-N-[(1S)-1-(5-fluoropyridin-2-yl)propyl]-3H-imidazo[4,5-b]pyridin-5-amine

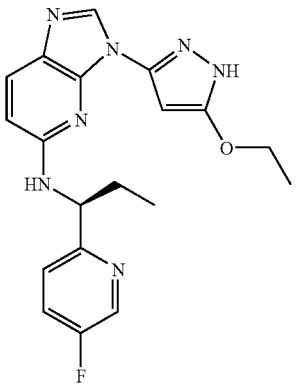 [SMILES: CCOc1cc(-n2cnc3ccc(N[C@@H](CC)c4ccc(F)cn4)nc32)n[nH]1]

The title compound was prepared using a procedure similar to the one described for the synthesis of Example 9 using $N^2$-(5-ethoxy-1H-pyrazol-3-yl)-$N^6$-[(1S)-1-(5-fluoropyridin-2-yl)propyl]-3-nitropyridine-2,6-diamine (Intermediate 59) as the starting material. LCMS: 382 [M+1]. $^1$H NMR (400 MHz, CD$_3$OD) δ 8.40 (s, 1H), 8.30 (s, 1H), 7.70 (d, 1H), 7.40 (d, 2H), 6.60 (d, 1H), 6.10 (br, 1H), 5.90 (s, 1H), 4.20 (q, 2H), 2.00 (m, 2H), 1.40 (d, 3H), 1.10 (t, 3H).

Example 24

3-(5-Isopropoxy-1H-pyrazol-3-yl)-N-[(1S)-1-pyrimidin-2-ylethyl]-3H-imidazo[4,5-b]pyridin-5-amine

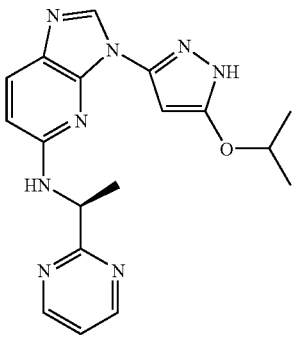 [SMILES: CC(C)Oc1cc(-n2cnc3ccc(N[C@@H](C)c4ncccn4)nc32)n[nH]1]

The titled compound was prepared using a procedure similar to the one described for the synthesis of Example 6 using $N^6$-[(1S)-1-(5-fluoropyrimidin-2-yl)ethyl]-$N^2$-(5-isopropoxy-1H-pyrazol-3-yl)-3-nitropyridine-2,6-diamine (Intermediate 20) as the starting material. The starting material (1.7 g) was dissolved into ethanol (10 mL). To the solution was added Pd—C (0.3 g, 10%). A hydrogen inlet was introduced into the reaction flask. The resulting mixture was stirred for 5 hours. Formamidine acetate (2 g) was added to the resulting mixture. The mixture was stirred at 85° C. for 4 hours. The resulting mixture was filtered, and the filtrate was concentrated. The resulting residue was separated by Silica gel column. The title compound was obtained (0.14 g) as a by-product. LCMS: 365 [M+1]. $^1$H NMR (400 MHz, CD$_3$OD) δ

8.60 (s, 2H), 8.20 (s, 1H), 7.60 (d, 1H), 7.20 (s, 2H), 6.50 (d, 1H), 6.10 (br, 1H), 5.10 (s, 1H), 4.70 (m, 1H), 1.40 (d, 3H), 1.30 (d, 6H).

Example 25

(S)-Ethyl 2-(1-(5-fluoropyridin-2-yl)ethylamino)-9-(5-methyl-1H-pyrazol-3-yl)-9H-purine-6-carboxylate

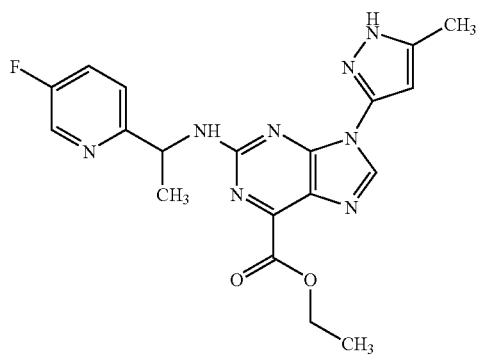 [SMILES: CCOC(=O)c1nc(NC(C)c2ccc(F)cn2)nc2c1ncn2-c1cc(C)[nH]n1]

The title compound was prepared according to the procedure described for Example 4 using Ethyl 2-{[(1S)-1-(5-fluoropyridin-2-yl)ethyl]amino}-6-[(5-methyl-1H-pyrazol-3-yl)amino]-5-nitropyrimidine-4-carboxylate (Intermediate 60) as the starting material. The title compound underwent decomposition shortly after its synthesis. LCMS: 411 [M+1]$^+$.

What is claimed is:

1. A compound, or a pharmaceutically acceptable salt thereof, wherein the compound has the structure:

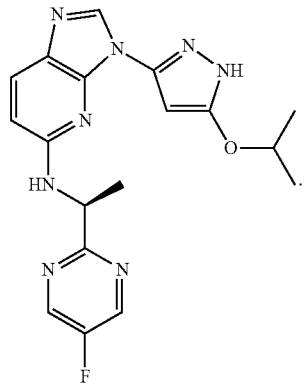 [SMILES: CC(C)Oc1cc(-n2cnc3ccc(N[C@@H](C)c4ncc(F)cn4)nc32)n[nH]1 ; "."]

2. The compound of claim 1.

3. A pharmaceutically acceptable salt of claim 1.

4. A pharmaceutical composition comprising a compound of claim 1, or a pharmaceutically acceptable salt thereof, and a pharmaceutically acceptable carrier, diluent or excipient.

* * * * *

UNITED STATES PATENT AND TRADEMARK OFFICE
CERTIFICATE OF CORRECTION

PATENT NO.       : 8,486,966 B2                                        Page 1 of 1
APPLICATION NO.  : 12/598473
DATED            : July 16, 2013
INVENTOR(S)      : Davies et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 817 days.

Signed and Sealed this

Eighth Day of September, 2015

Michelle K. Lee
*Director of the United States Patent and Trademark Office*